US011304877B2

(12) United States Patent
Strawder

(10) Patent No.: US 11,304,877 B2
(45) Date of Patent: Apr. 19, 2022

(54) METHOD AND APPARATUS FOR ASSISTING, CHECKING, AND CONFIRMING NASOGASTRIC AND OROGASTRIC TUBE INSERTION AND PLACEMENT

(71) Applicant: Glenn Gerald Strawder, Burtonsville, MD (US)

(72) Inventor: Glenn Gerald Strawder, Burtonsville, MD (US)

(*) Notice: Subject to any disclaimer, the term of this patent is extended or adjusted under 35 U.S.C. 154(b) by 0 days.

(21) Appl. No.: 17/331,966

(22) Filed: May 27, 2021

(65) Prior Publication Data
US 2021/0369571 A1 Dec. 2, 2021

Related U.S. Application Data

(60) Provisional application No. 63/102,081, filed on May 27, 2020.

(51) Int. Cl.
*A61J 15/00* (2006.01)
(52) U.S. Cl.
CPC ....... *A61J 15/0026* (2013.01); *A61J 15/0003* (2013.01); *A61J 15/0084* (2015.05)
(58) Field of Classification Search
CPC . A61J 15/0026; A61J 15/0084; A61J 15/0003
USPC ......................................................... 604/516
See application file for complete search history.

(56) References Cited

U.S. PATENT DOCUMENTS

| 4,381,011 A | 4/1983 | Somers, 3rd |
| RE32,306 E | 12/1986 | Waters |
| 5,085,216 A | 2/1992 | Henley, Jr. et al. |
| 5,379,779 A | 1/1995 | Rowland et al. |
| 2004/0068190 A1* | 4/2004 | Cespedes ............... A61B 8/12 600/466 |
| 2006/0100492 A1* | 5/2006 | Hartle ............... A61B 5/14539 600/350 |
| 2006/0189947 A1 | 8/2006 | Gilbert et al. |
| 2009/0187164 A1 | 7/2009 | Rowe |
| 2014/0163528 A1 | 6/2014 | Heyns et al. |
| 2016/0331646 A1 | 11/2016 | Thomas |

FOREIGN PATENT DOCUMENTS

WO WO-2012046087 A1 * 4/2012 ............ A61M 16/04

* cited by examiner

*Primary Examiner* — Phillip A Gray
(74) *Attorney, Agent, or Firm* — Thomas P. O'Connell; O'Connell Law Firm

(57) ABSTRACT

A long, thin, flexible medical apparatus, a kit including such an apparatus, and a method for employing the apparatus to assist in placing a distal portion of a lumen of a gastric tube in a stomach of a mammal. The apparatus comprises an elongate body portion, a handle portion fixed to a proximal end of the body portion, and a distal tip portion fixed to a distal end of the body portion. An ability to insert the body and distal tip portions into the gastric tube over the length of the long, thin, flexible structure provides a positive indication that the lumen is not blocked, obstructed, or otherwise compromised over that length. pH indicator sensors may be retained by the distal tip portion to exhibit a verifiable color change in response to contact with a predetermined subject fluid, such as gastric fluid, lung fluid, or another bodily fluid.

33 Claims, 8 Drawing Sheets

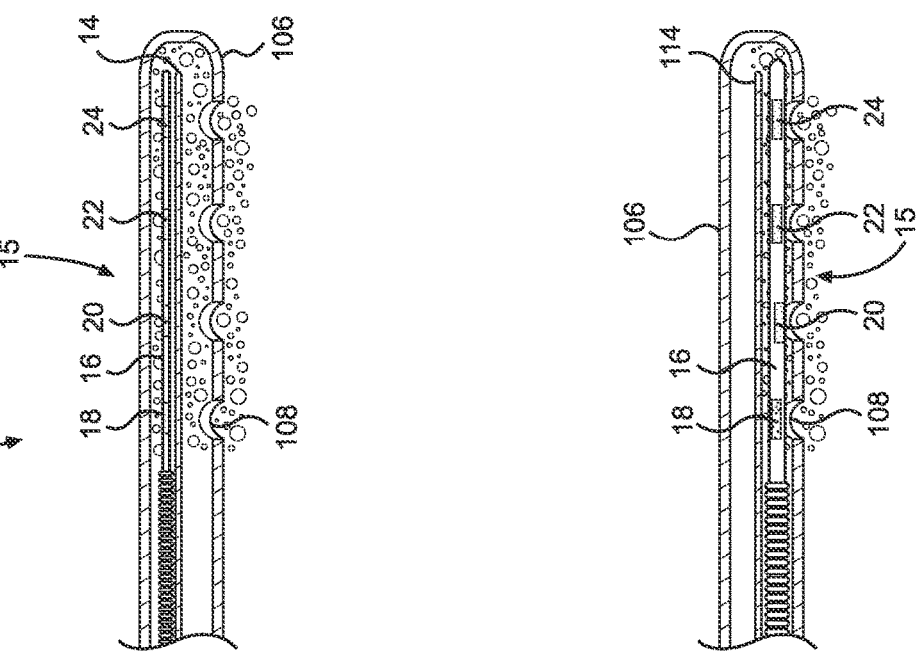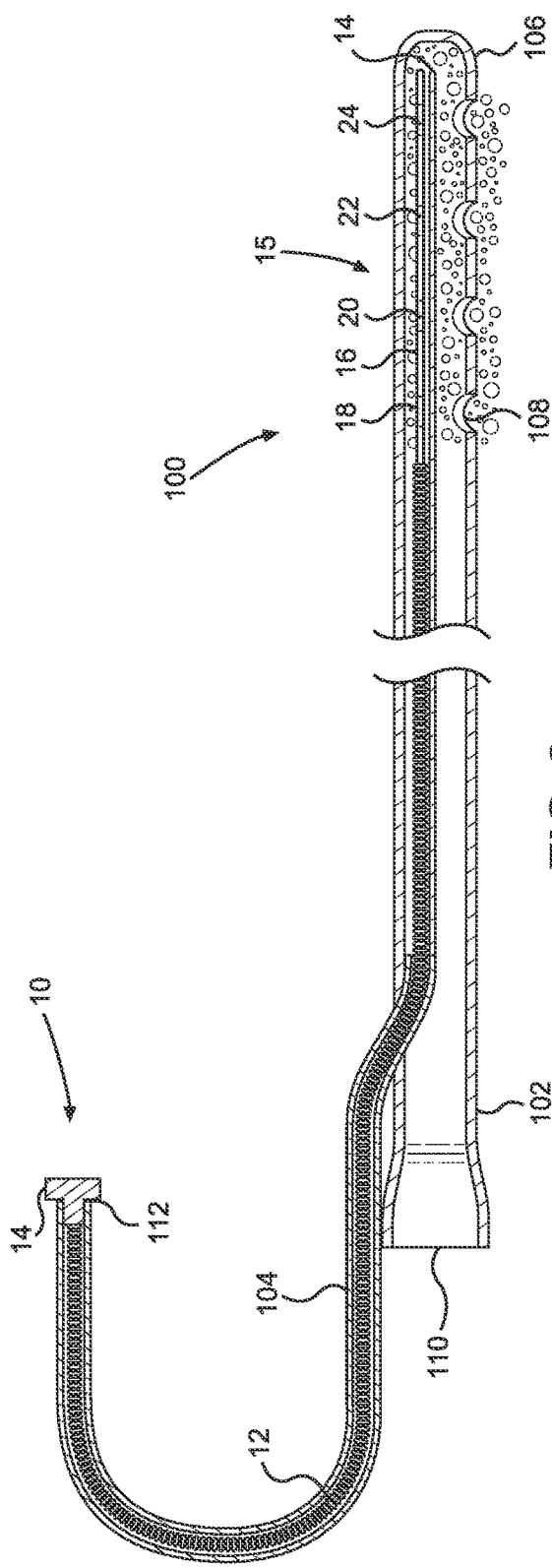

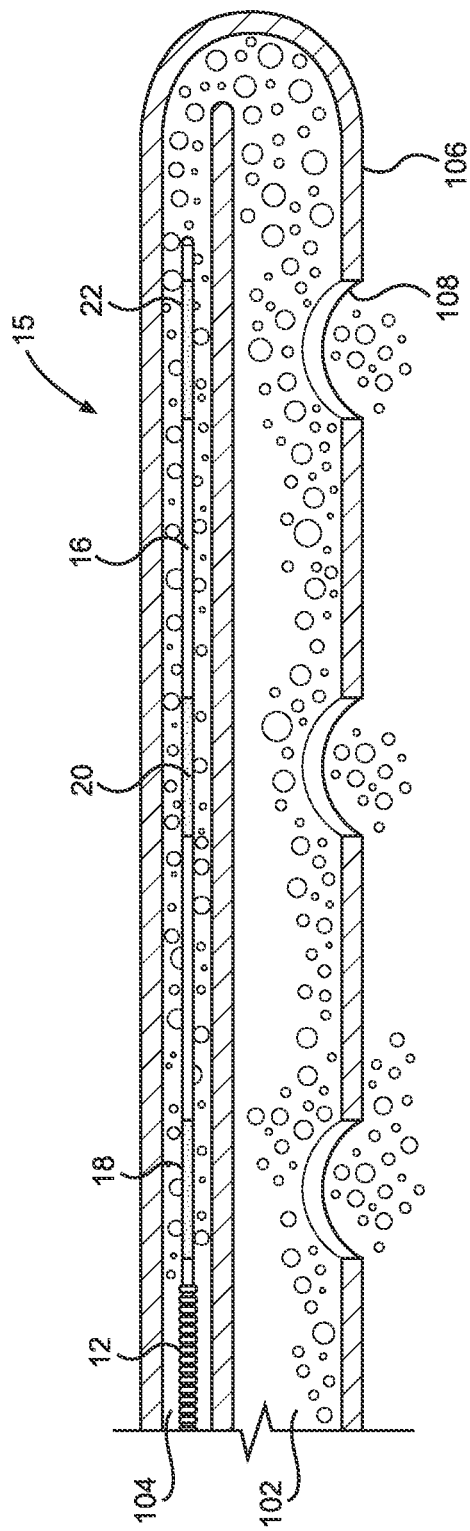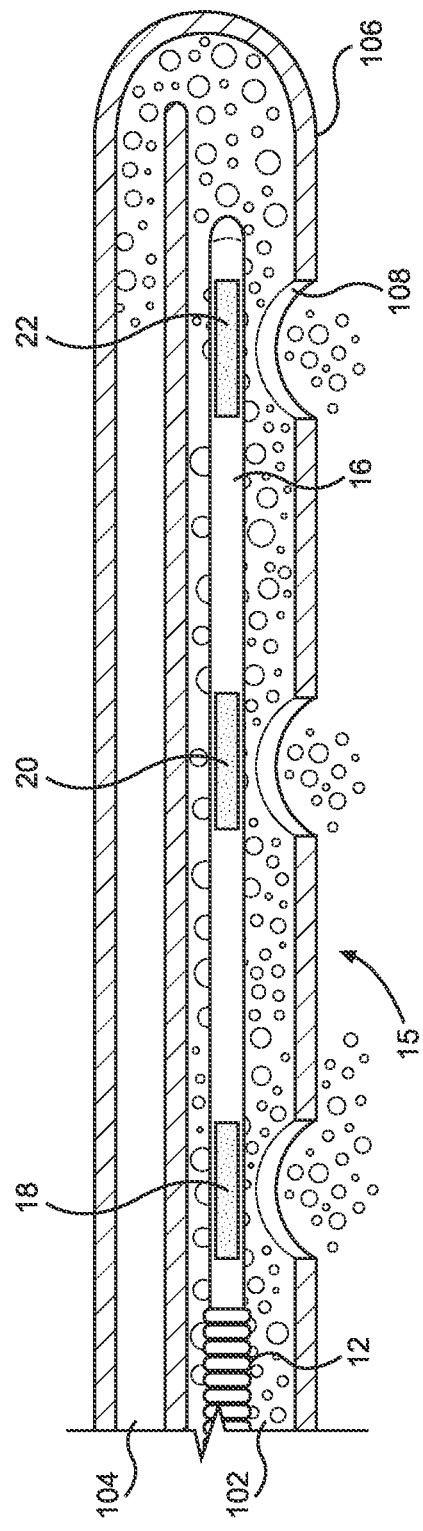
FIG. 5
FIG. 6

METHOD AND APPARATUS FOR ASSISTING, CHECKING, AND CONFIRMING NASOGASTRIC AND OROGASTRIC TUBE INSERTION AND PLACEMENT

CROSS REFERENCE TO RELATED APPLICATION

This application claims priority to and the benefit of U.S. Provisional Patent Application Ser. No. 63/102,081, filed May 27, 2020, which is entitled, "Long Flexible Structure for Confirming Placement of an NG Tube in the Stomach" and which is incorporated herein by reference in its entirety.

FIELD OF THE INVENTION

The present invention relates generally to nasogastric and orogastric tubes and the insertion and placement thereof. More particularly, disclosed herein is an apparatus for assisting a nasogastric or orogastric tube in traversing the tortuous terrain from the nose or mouth of a subject to the stomach and in checking whether a compromise, such as a bend, a kink, a twist, a coil, or a loop, has been formed in the tube during the insertion and, if not, confirming whether the distal portion of the tube is indeed inside the stomach, each performed rapidly and without a need for x-ray imaging.

BACKGROUND OF THE INVENTION

Nasogastric and orogastric tubes are tools used in medicine for diagnostic and therapeutic purposes, such as the removal of contents from the stomach, including air, small solid objects, and fluids such as poison, to decompress the stomach, and to put substances directly into the stomach, including nutrients and medicines when a person cannot take food or drink by mouth.

Nasogastric or orogastric intubation is a medical procedure involving the blind insertion of an extremely flexible tube through the nose or mouth of a mammal, down the roughly 90-degree turn at the back of the mouth, through the pharynx, through the esophagus, and into the stomach or upper small intestinal tract. The diameter, length, and tortuousness of the terrain to be traversed play a major role in how problematic and challenging the insertion attempt will be in humans and other mammals.

Nasogastric and orogastric tubes are typically made of synthetic rubber or nonreinforced polymer plastic materials. They are, therefore, prone to veering off track or becoming compromised somewhere inside a person during and after insertion. A further challenge with nasogastric and orogastric tubes is that, since the lower end of the tubes are blindly inserted in and beyond the nose or mouth of a subject, there is no way for the user to know if and when the lower end of the tube has reached its intended destination.

It is commonly necessary under present practices to use x-ray imaging to confirm the placement of gastric tubes after insertion. However, the use of x-rays is not without its own problems. By way of example and not limitation, it is time consuming, expensive, and potentially harmful to patients based on the need for radiation.

It is apparent, therefore, that there is a real need for a faster, more economical, and less harmful way by which the insertion of a nasogastric or orogastric tube can be accomplished and confirmed. Indeed, numerous articles have been written regarding the risks and difficulties inherent in placing nasogastric and orogastric tubes. Particularly since the individuals that need such tubes are in or are approaching a crisis situation, it is vital in the medical field to have available an apparatus that can assist in, detect, and confirm the placement of nasogastric and orogastric tubes effectively, efficiently, without high costs, and with a minimized risk of harm to the patient.

SUMMARY OF THE INVENTION

The composition of a nasogastric and orogastric tube makes them extremely vulnerable and prone to deviate off course or otherwise to become compromised during insertion when they encounter the standard anatomical friction or resistance points as they pass through the nose or mouth and into the stomach. The lower ends of nasogastric and orogastric tubes lead the way during insertion, and those lower ends may veer off course or become compromised when they cannot overcome an encounter with the standard anatomical friction or resistance points along the insertion path. Veering off course when the lower end cannot overcome an encounter means following the path of least resistance. Too often, that path leads into a lung due to the proximity of the larynx and the esophagus. In other circumstances, the tube may become compromised when the lower end cannot overcome an encounter or veers off course such that the lower end surrenders to losing its integrity and bends, kinks, twists, coils, or loops thereby rendering the tube useless.

With a knowledge of the foregoing, the present inventor has appreciated that the lower ends of nasogastric and orogastric tubes need added firmness during insertion sufficient to assist the lower end in overcoming the tube's tendency to deviate or compromise upon encountering the standard points of friction and resistance during insertion.

The present inventor has further appreciated that all forms of compromise, including bending, kinking, twisting, coiling, and looping, tend to reduce the inner diameter of each lumen of a nasogastric and orogastric tube at the same time, in the same manner, and at the same location. Most, if not all, forms of compromise cause the passageway of a lumen to collapse inwardly, which reduces the effective inner diameter of the lumen. The amount by which the inner diameter of the lumen is reduced depends entirely on the amount or degree of the compromise.

Reducing the effective inner diameter of a lumen of a nasogastric or orogastric tube to a compromised size smaller than the diameter of a solid object within the lumen causes the passageway of the lumen to shrink down and pinch or squeeze tightly on the solid object therewithin. Restrictive force may be applied to the object sufficient to prevent a user from being able to move the object beyond the reduction, at least not without significant resistance without obstruction. Additionally, reducing the effective inner diameter of a lumen of a nasogastric or orogastric tube to a compromised size smaller than the diameter of a solid object prior to attempting to pass the object through the lumen will tend to prevent a user from being able to cause the solid object to travel through or past the reduction.

In view of the dangers, limitations, and potential complications deriving from nasogastric or orogastric tubes of the prior art, a goal of the present invention is to provide a method and apparatus capable of assisting the lower end of a nasogastric or orogastric tube in overcoming the tendency of such tubes to deviate or collapse when encountering points of anatomical friction or resistance during insertion.

A further goal of the present invention is to provide a method and apparatus that enable a user to verify whether the lumen of a nasogastric or orogastric tube is obstructed or has otherwise become compromised, such as during or after the insertion process.

Another goal of the present invention to provide a method and apparatus capable of confirming whether the lower end of a nasogastric or orogastric tube is successfully positioned in the stomach.

These and further objects and advantages of the present invention will become obvious not only to one who reviews the present specification and drawing but also to those who have an opportunity to experience embodiments of the method and apparatus disclosed herein in operation. It will be appreciated that, although the accomplishment of each of the foregoing objects in a single embodiment of the invention may be possible and indeed preferred, not all embodiments will seek or need to accomplish each and every potential advantage and function. Nonetheless, all such embodiments should be considered within the scope of the present invention.

In one manifestation, the invention can be characterized as an apparatus for assisting in the placement of a distal portion of a lumen of a gastric tube, such as a nasogastric tube or an orogastric tube, in a stomach of a mammal. In this context, reference to assisting should be interpreted to include assisting, checking, and confirming nasogastric and orogastric tube insertion and placement. The apparatus can be considered to be founded on an elongate body portion of flexible material with a proximal end and a distal end. By way of non-limiting example, the body portion can take the form of an elongate core surrounded by a sheath. A handle portion is fixed to the proximal end of the body portion. The handle portion has a width. In certain practices of the invention, the width of the handle portion can be equal to or greater than a width of the body portion, although other dimensional relationships are possible. A distal tip portion is fixed to the distal end of the body portion, whether by being integrally formed therewith or as a separate member coupled thereto. The body portion and the distal tip portion together form a long, thin, flexible structure with a length for being selectively received into a passageway of a lumen of the gastric tube. Under such constructions, an ability to insert the body portion and the distal tip portion into the passageway in the lumen of the gastric tube over the length of the long, thin, flexible structure provides a positive indication that the lumen is not blocked, obstructed, or otherwise compromised over the length of the long, thin, flexible structure.

In embodiments of the apparatus, the distal tip portion of the apparatus has rigidity sufficient, when received into the distal portion of the lumen of the gastric tube, to facilitate passage of the distal portion of the lumen during insertion into the mammal. Also according to embodiments of the invention, the body portion and the distal tip portion of the apparatus can have lateral dimensions sufficient to prevent passage of the body portion and the distal tip portion past a blockage, obstruction, or other compromise in the lumen of the gastric tube. Also as disclosed herein, the body portion and the distal tip portion of the apparatus can have lateral dimensions sufficient to prevent retraction of the body portion and the distal tip portion when the body portion and the distal tip have been received into the lumen of the gastric tube and a compromise develops in the lumen of the gastric tube at a location along the length of the long, thin, flexible structure.

In certain embodiments, a pH indicator sensor array is retained by the long, thin, flexible structure formed by the body portion and the distal tip portion. The pH indicator sensor array comprises at least a first pH indicator sensor with a pH indicator. The first pH indicator sensor is calibrated to exhibit a verifiable color change in response to contact with a predetermined subject fluid, such as gastric fluid, lung fluid, or another fluid.

It is further disclosed herein that the pH indicator sensor array can additionally comprise a second pH indicator sensor with a pH indicator calibrated to exhibit a verifiable color change in response to contact with a predetermined subject fluid. The first and second pH indicator sensors can, for instance, be calibrated to exhibit a verifiable color change in response to contact with the same predetermined subject fluid. In other embodiments, the first and second pH indicator sensors can be calibrated to exhibit a verifiable color change in response to contact with different predetermined subject fluids, such as with the first pH indicator sensor calibrated to exhibit a verifiable color change in response to contact with gastric fluid and the second pH indicator sensor calibrated to exhibit a verifiable color change in response to contact with lung fluid.

Still further, the pH indicator sensor array retained by the long, thin flexible structure can comprise a plurality of pH indicator sensors, each with a pH indicator calibrated to exhibit a verifiable color change in response to contact with a predetermined subject fluid. The plurality of pH indicator sensors can be longitudinally spaced along the long, thin, flexible structure to facilitate alignment of the sensors with eyelet openings disposed in the distal portion of the lumen of the gastric tube.

The apparatus can further include measurement markings disposed along the long, thin, flexible structure. For example, measurement markings can be disposed to descend along the long, thin, flexible structure from a highest number disposed adjacent to the proximal end of the body portion. Under such constructions, the measurement markings can facilitate a determination of a longitudinal location of a blockage, obstruction, or other compromise of the gastric tube inside the mammal.

In certain practices of the invention, at least one notch can be disposed in the long, thin, flexible structure. The at least one notch demonstrates decreased resistance to flexion in comparison to segments of the long, thin, flexible structure disposed adjacent to the notch.

Also as disclosed herein, at least one longitudinal or lateral reinforcing rib can be disposed on the long, thin, flexible structure. The reinforcing rib is operative to increase the local thickness and rigidity of the long, thin, flexible structure.

Embodiments of the invention can alternatively be characterized as a kit for assisting in a placement of a distal portion of a lumen of a gastric tube in a stomach of a mammal. The kit comprises a gastric tube comprising a lumen with an entrance, a passageway, and a distal portion and a long, thin, flexible medical apparatus. The apparatus is again founded on an elongate body portion of flexible material with a proximal end and a distal end. A handle portion is fixed to the proximal end of the body portion. The handle portion has a width greater than a width of the body portion. A distal tip portion is fixed to the distal end of the body portion, and the body portion and the distal tip portion together form a long, thin, flexible structure with a length for being selectively received into a passageway of a lumen of the gastric tube. With such a kit provided, an ability to insert the body portion and the distal tip portion into the passageway in the lumen of the gastric tube over the length of the long, thin, flexible structure provides a positive indication that the lumen is not blocked, obstructed, or otherwise compromised over the length of the long, thin, flexible structure.

In certain embodiments of the kit, a pH indicator sensor array can be retained by the long, thin flexible structure. That array could comprise a single sensor, or it may comprise a plurality of pH indicator sensors, each with a pH indicator calibrated to exhibit a verifiable color change in response to contact with a predetermined subject fluid. For instance, the plurality of pH indicator sensors can be longitudinally spaced along the long, thin, flexible structure. Moreover, the distal portion of the lumen of the gastric tube can have a plurality of apertures spaced therealong. The plurality of pH indicator sensors of the pH indicator sensor array can be disposed to align with the plurality of apertures in the distal portion of the gastric tube when the long, thin, flexible structure is inserted into the lumen of the gastric tube.

The passageway of the lumen of the gastric tube has a length, and the length of the long, thin, flexible structure formed by the body portion and the distal tip portion in certain embodiments of the apparatus does not exceed the length of the passageway of the lumen. In certain examples, for instance, the length of the long, thin, flexible structure formed by the body portion and the distal tip portion is approximately equal to the length of the passageway of the lumen. As used herein, approximately equal should be interpreted to include the long, thin, flexible structure being equal in length to the length of the passageway of the lumen or within an insubstantial margin longer or shorter than the length of the passageway.

In particular embodiments of the apparatus, the length of the long, thin, flexible structure formed by the body portion and the distal tip portion could be greater than the length of the passageway of the lumen in which it is to be inserted. In such practices of the invention and while recognizing that it could be greater in lateral dimension, the handle portion could, again by way of example and not limitation, be equal or perhaps even smaller in lateral dimension as compared to the lateral dimension of the body portion since the apparatus could not fall inside the lumen to become irretrievable, trapped, or stuck inside the lumen. Although not excluded from the scope of the claims except where expressly stated, the length of the long, thin, flexible structure formed by the body portion and the distal tip portion will preferably not be substantially less than the length of the passageway of the lumen in which it is to be inserted. Where the length of the long, thin, flexible structure formed by the body portion and the distal tip portion is longer than the length of the passageway of the lumen, the body portion and the distal tip portion will preferably have a measurement scale with numbering descending from the proximal end of the body portion along the long, thin, flexible structure. With such a measurement scale provided, a user can be apprised of when the actual length of the passageway of the lumen has been traversed. Once the actual length of the passageway of the lumen has been traversed, the user can cease further insertion knowing that the distal tip portion and the body portion have travelled sufficient distance to prove there is not blockage, obstruction, or other compromise in the lumen.

Practices of the invention can be characterized still further as a method for assisting in a placement of a distal portion of a lumen of a gastric tube in a stomach of a mammal. The method includes providing a gastric tube comprising a lumen with an entrance, a passageway, and a distal portion and providing a long, thin, flexible medical apparatus. The long, thin, flexible medical apparatus comprises an elongate body portion of flexible material, a handle portion fixed to a proximal end of the body portion, and a distal tip portion fixed to a distal end of the body portion. The body portion and the distal tip portion together form a long, thin, flexible structure with a length for being selectively received into a passageway of a lumen of the gastric tube. The method further comprises inserting the lumen of the gastric tube into the mammal. Then, one can determine whether the distal portion of the lumen of the gastric tube is placed without blockage, obstruction, or other compromise in the stomach of the mammal based on an insertion of the long, thin, flexible structure into the lumen of the gastric tube.

The step of determining whether the distal portion of the lumen of the gastric tube is placed without blockage, obstruction, or other compromise in the stomach of the mammal can, in certain practices, comprise determining whether the long, thin, flexible structure is capable of being fully received into the lumen of the gastric tube without restriction by blockage, obstruction, or other compromise. In further practices of the method, the step of determining whether the distal portion of the lumen of the gastric tube is placed without blockage, obstruction, or other compromise in the stomach of the mammal can be carried out by determining whether the long, thin, flexible structure when received into the lumen of the gastric tube can be advanced or retracted without restriction by blockage, obstruction, or other compromise.

In other practices of the method, a pH indicator sensor array is retained by the long, thin, flexible structure formed by the body portion and the distal tip portion. The pH indicator sensor array comprises a first pH indicator sensor with a pH indicator calibrated to exhibit a verifiable response to contact with a predetermined subject fluid. In such practices of the method, the step of determining whether the distal portion of the lumen of the gastric tube is placed in the stomach of the mammal comprises determining whether the pH indicator exhibits the verifiable response.

It is still further disclosed herein that the pH indicator sensor array retained by the long, thin flexible structure can include a second pH indicator sensor with a pH indicator calibrated to exhibit a verifiable color change in response to contact with a predetermined subject fluid. For instance, the first and second pH indicator sensors can be calibrated to exhibit a verifiable color change in response to contact with different predetermined subject fluids, such as with the first pH indicator sensor calibrated to exhibit a verifiable color change in response to contact with gastric fluid and the second pH indicator sensor calibrated to exhibit a verifiable color change in response to a bodily fluid other than gastric fluid, such as but not limited to lung fluid.

Also as disclosed herein, measurement markings can be disposed along the long, thin, flexible structure. In such embodiments, the step of determining whether the distal portion of the lumen of the gastric tube is placed without blockage, obstruction, or compromise in the stomach of the mammal based on an insertion of the long, thin, flexible structure at least partially into the lumen of the gastric tube includes determining a location of a blockage, obstruction, or compromise in the gastric tube based on the measurement markings disposed along the long, thin, flexible structure.

One will appreciate that the foregoing discussion broadly outlines the more important goals and certain features of the invention to enable a better understanding of the detailed description that follows and to instill a better appreciation of the inventor's contribution to the art. Before any particular embodiment or aspect thereof is explained in detail, it must be made clear that the following details of construction and

BRIEF DESCRIPTION OF THE DRAWINGS

FIG. 3 is a partially-sectioned cross-sectional view of an apparatus according to the invention fully inserted into a secondary lumen;

FIG. 4 is a cross-sectional view of an apparatus as disclosed herein fully inserted in a main lumen;

FIG. 5 is an amplified cross-sectional view of an apparatus according to the invention disposed within a secondary lumen with gastric fluid making contact with the pH indicator sensors of the apparatus;

FIG. 6 is an amplified cross-sectional view of an apparatus according to the present invention with gastric fluid making contact with pH indicator sensors of the apparatus aligned with eyelet openings of an NG tube;

DETAILED DESCRIPTION OF PREFERRED EMBODIMENTS

Figure 1:
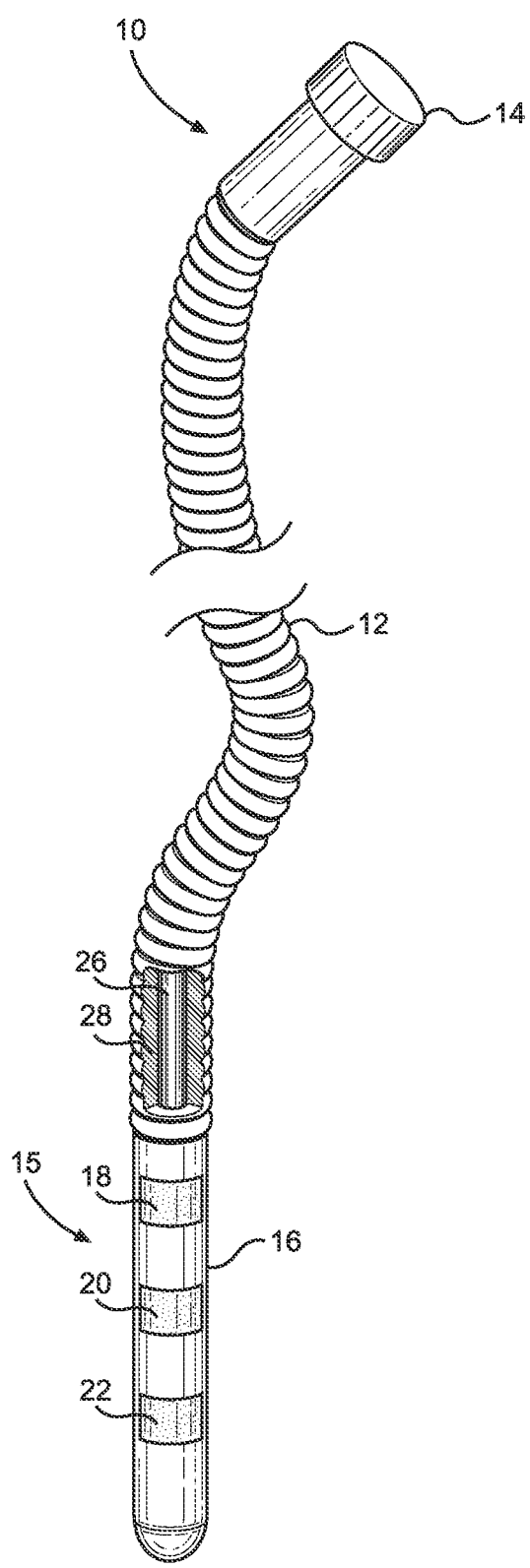
FIG. 1 is a view in front elevation of an embodiment of the apparatus of the present invention wherein pH indicator sensors are disposed in longitudinal alignment along a distal tip portion thereof.

Methods and apparatuses for assisting, checking, and confirming nasogastric and orogastric tube insertion and placement as disclosed herein can pursue a wide variety of embodiments, each within the scope of the invention. However, to ensure that one skilled in the art will be able to understand and, in appropriate cases, practice the present invention, certain preferred embodiments and aspects of the broader invention revealed herein are described below and shown in the accompanying drawing figures.

The present invention was made to meet the previously unsolved need for a method and apparatus by which the insertion of a nasogastric or orogastric tube in a subject can be readily assisted, checked, and confirmed in a rapid and efficient manner without a need for x-rays. The methods and apparatuses disclosed herein are at times shown and described with respect to the insertion of a nasogastric or NG tube in the stomach of a person. However, the present invention shall not be considered to be so limited except as may be expressly provided for in the claims. It will be understood, for instance, that the present invention has equal application to orogastric tubes and with respect to all mammals. Collectively, orogastric tubes and nasogastric tubes may be referred to as gastric tubes herein.

The structure of a typical NG tube can be further understood with reference to FIGS. 3 and 4 where the NG tube is indicated generally at 100. Also in FIGS. 3 and 4, an apparatus according to the present invention is selectively received into the NG tube 100 and indicated generally at 10.

Many such NG tubes 100 have two types of lumens: a main lumen 102 and a secondary lumen 104. The main lumen 102 has a distal or lower end 106 and an entrance aperture 110. The secondary lumen 104 has an entrance aperture 112, a proximal portion free of the main lumen 102, and a distal portion that extends within the main lumen 102. Lumens 102 and 104 of NG tubes 100 vary in inner and outer diameters, shape, and the length of the passageway therethrough. The main lumen 102 of most nasogastric tubes 100 is called the 'suction or drainage lumen' and occupies the largest space of the tube 100. The distal or lower portion 106 of the main lumen 102 and the NG tube 100 in general typically has multiple eyelet openings 108 for inputting and removing fluids and solid substances relative to the stomach quickly.

The secondary lumens 104 of nasogastric tubes 100 are used for many different purposes. The distal portion of the secondary lumen 104 occupies a longitudinal, relatively narrow diameter space of the tube 100. The distal portion of the secondary lumen 104 has at least one opening 114 to be in fluidic communication with the main lumen 102. As such, the sidewall of the distal portion of the secondary lumen 104 opens into the passageway of the main lumen 102 of the NG tube 100 within the distal portion 106 of the NG tube 100. As disclosed herein, the sidewall and the distal portion opening 114 allow fluid that enters the eyelet openings 108 in the distal portion 106 from the outside surroundings to pass. When the apparatus 10 of the present invention is fully inserted into the NG tube 100 with a distal tip portion 16 thereof disposed within the distal portion 106 of the lumen 100, liquid received into the distal portion 106 of the NG tube 100 will contact the distal tip portion 16 of the present apparatus 10.

As referenced herein, the inner diameter of a lumen 102 or 104 of a nasogastric tube 100 may be considered as the measurement across the inside of the lumen 102 or 104. That inner diameter of a lumen 102 or 104 is less than the outer diameter of the same lumen 102 or 104. The inner diameter of the main lumen 102 of most NG tubes 100 is greater than the inner diameter of the secondary lumen 104 of the same tube 100. In most NG tubes 100, the main lumen 102 has a larger inner diameter along an upper or proximal and middle passageway and a smaller inner diameter for the lower or distal passageway. In some NG tubes 100, the main lumen 102 has the same inner diameter at the proximal and middle passageways as in the distal passageway. The inner diameters of the main lumen 102 and the secondary lumen 104 of NG tubes 100 is often not disclosed by the manufacturer.

Nasogastric tubes 100 are commonly sized by their outer diameter in "FR" units or "French units". FR units are a gauge measurement known in the art where one increment on the FR scale is equal to ⅓ of a millimeter. Thus, an 8 FR catheter or nasogastric tube 100 is 8×0.33 mm or 2.64 mm. Typically, standard nasogastric tube outer diameter measurements are 4 FR to 8 FR for the neonatal range, 6 FR to 14 FR for children, and 12 FR to 18 FR for adults.

The overall length of a chosen nasogastric tube 100 depends entirely on the subject, whether the person be a newborn, an infant, child, an adolescent, or an adult, with whom it is intended to be used. Typical lengths range from 6 inches to 6 feet. For example, nasogastric tubes 100 with overall lengths from 21.5 to 39 inches are designed for small children, and tubes 100 with overall lengths from 42 to 50 inches are designed for adults.

The selection process to determine the length of an NG tube 100 to use for newborns, infants, children, adolescents, and adults is similar and is performed by a standard method of measuring the distance from the tip of the nose of the person, around one ear, and down to just below the left costal margin or region of the individual's chest. The selection process to determine the outer diameter of an NG tube 100 to use for newborns, infants, children, adolescents and adults is determined by the size of the opening of the nose of the person into whom the tube is to be inserted.

With combined reference to FIGS. 1 through 4, for instance, embodiments of the apparatus 10 of the present invention can be seen to be founded on an elongate body portion 12. A handle portion 14 is fixed to a proximal end of the body portion 12, and a distal tip portion 16 is fixed to the distal end of the body portion 12. The body portion 12, the handle portion 14, and the distal tip portion 16 could be separately formed and fixed to one another, or two or more of the body portion 12, the distal tip portion 16, and the handle portion 14 could be integrally formed in certain practices of the invention. With the elongate body portion 12, the apparatus 10 may alternatively be referred to as a long, thin, flexible medical device (LTFMD) 10. As taught herein, the LTFMD 10 uniquely works in concert with the main or secondary lumen 102 or 104 of a nasogastric or orogastric tube 100.

According to the invention, the LTFMD 10 can be contoured and configured to perform at least three different and useful tasks while inside the lumen 102 or 104 of an NG tube 100. The first task is to assist the distal portion 106 of the NG tube 100 to traverse the terrain during insertion. The second task is to check the passageway of a lumen 102 or 104 for a blockage or compromise. The third task is to confirm whether the distal portion 106 of the NG tube 100 is inside the stomach as intended. A LTFMD 10 can be designed to perform each task individually or in any combination.

The body portion 12 and potentially the distal tip portion 16 of the LTFMD 10 can be cylindrical, hexagonal, octagonal, or any other shape that will allow the LTFMD 10 to properly perform one or more of the tasks above inside the lumen 102 or 104 of the NG tube 100 into which it is to be inserted. The components of the LTFMD 10 can be made completely or partially of materials commonly employed in the medical device field, such as, but not limited to metals, polymers, synthetic rubbers, combinations thereof.

Potential metals for the LTFMD 10 and particularly the body portion 12 and the distal portion 16 thereof could include, but again are not limited to, aluminum, solid steel or nitinol core wires, and solid core wire wrapped in a smaller wire coil or braid. Coiled or braided wires offer a large amount of flexibility, longitudinal pushing force, and kink resistance. Nitinol is highly elastic and offers good flexibility and torque in tortuous anatomy and pathways. These materials allow the apparatus 10 to have similar flexibility as that of a nasogastric tube 100 while traversing the terrain during insertion. Concomitantly, the body portion 12 of the LTFMD 10 adds rigidity and firmness sufficient to assist the tube 100 to maintain integrity and to not collapse during insertion.

Potential polymers for the LTFMD 10 and particularly the body portion 12 and the distal tip portion 16 thereof could include, but again are not limited to, natural and synthetic rubber, polyurethanes, silicone, and other polymeric materials. Embodiments of the LTFMD 10 are contemplated wherein solid or braided steel or nitinol wires are coated with a polymer such as, but not limited to, silicone or polytetrafluoroethylene (PTFE), to increase lubricity. Further, hydrophilic coatings may be applied to reduce friction during deployment and to ease movement in tortuous pathways. The body portion 12 and the distal tip portion 16 could have smooth or textured surfaces. In the depicted embodiments of FIGS. 1 and 2, for instance, the distal tip portions 16 are smooth while the body portions 12 have ribbed exterior surfaces.

The above metals and polymers give the LTFMD 10 the ability to be inserted and to traverse the passageway of the lumens 102 and 104 of an NG tube 100 smoothly and without resistance, fracturing, or breaking.

Figure 2:
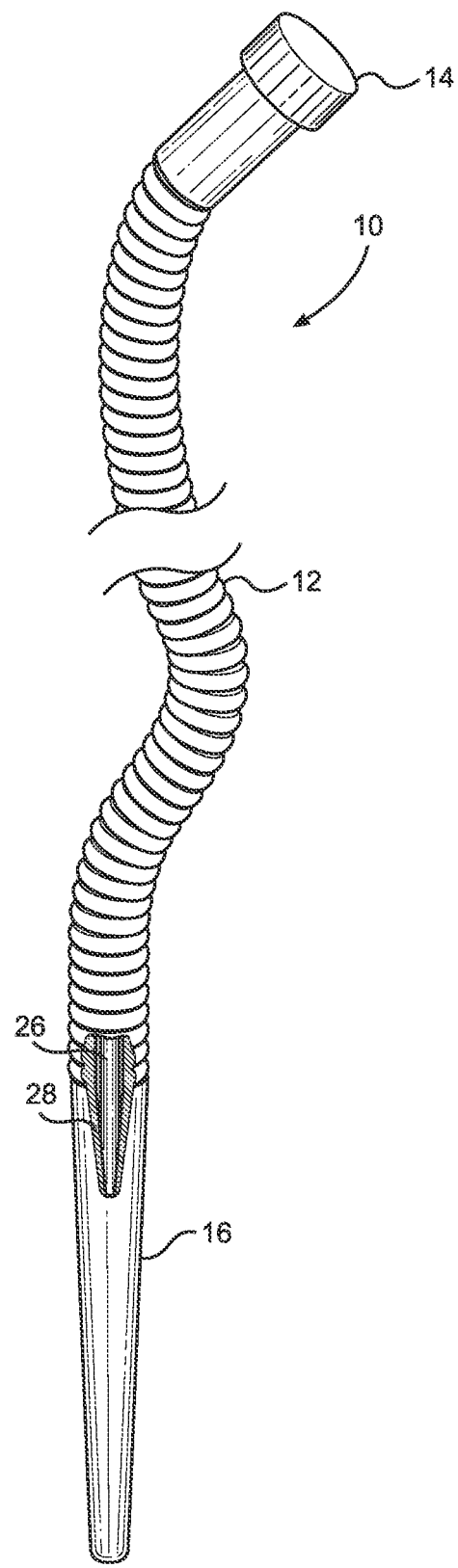
FIG. 2 is a partially-sectioned view in front elevation of an embodiment of the apparatus wherein the distal tip portion thereof is tapered.
Figure 7:
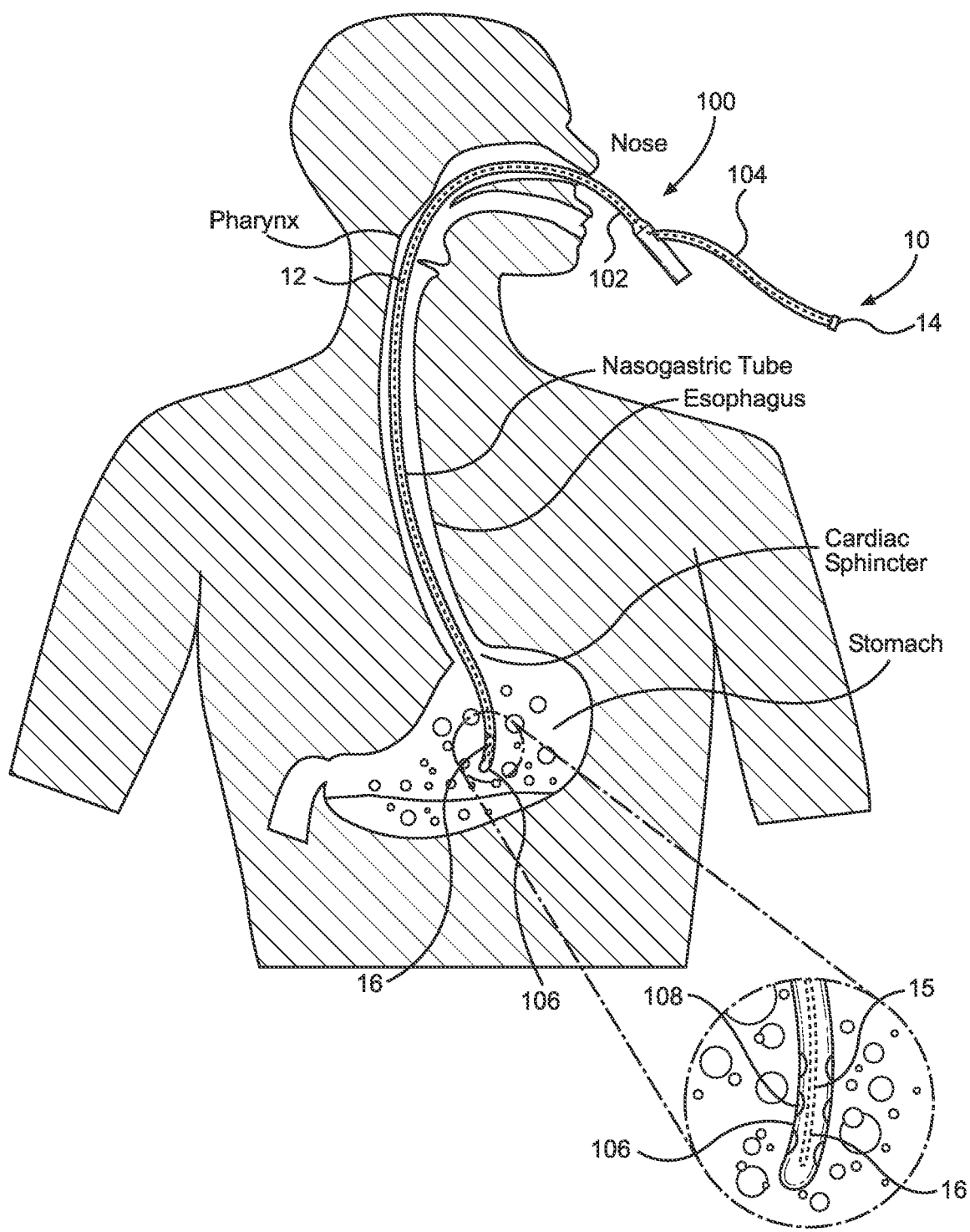
FIG. 7 is a view of an apparatus pursuant to the invention inserted in a secondary lumen of an NG tube placed in a human stomach.

In practices of the invention and with particular reference to FIGS. 1 and 2, the LTFMD 10 may have a core 26 of metal or plastic. In one embodiment, for instance, the core 26 may be of nitinol. In embodiments of the LTFMD 10, the nitinol core 26 may be surrounded by a laterally-ribbed sheath 28, which could be of a polymer, such as but not limited to a polymer selected from synthetic rubber or polyurethane.

As set forth above, the handle 14 of the LTFMD 10 is fixed to the proximal end of the body portion 12. A distal portion of the handle 14 is attached to the proximal end of the body portion 12 while the opposite, proximal portion of the handle 14 is free and not attached to anything. The proximal portion of the handle 14 is wider than the diameter of the proximal end of the body portion 12. The proximal portion of the handle 14 is also crafted to be wider than the diameter of the entrance aperture 110 or 112 of the lumen 102 or 104 of the NG tube 100 into which the LTFMD 10 is to be inserted. The wider diameter of the proximal portion of the handle 14 eliminates the possibility of the body portion 12 and the distal tip portion 16 falling inside a lumen 102 or 104 and becoming irretrievable, trapped, or stuck inside.

In some embodiments, the handle 14 is configured so that a user is able to use a thumb and index finger to grip and control movement of the LTFMD 10 during insertion or removal from a lumen 102 or 104. In some embodiments, the handle 14 is configured so that a user is able to use a thumb, index finger and middle finger to grip and control movement of the LTFMD 10 during insertion or removal from a lumen 102 or 10.

The body portion 12 of the LTFMD 10 is uniquely contoured and configured to traverse the upper and middle passageways of the main or secondary lumens 102 or 104 of an NG tube 100 in which the LTFMD 10 is intended to be fully inserted.

The outer diameter of the body portion 12 of a LTFMD 10 may be dependent on the inner diameter of the lumen 102 or 104 of the NG tube 100 into which it is intended to be inserted and the intended task or purpose of the apparatus 10. However, the outer diameter of the body portion 12 of the LTFMD 10 is preferably small enough to allow the body portion 12 to traverse the upper and middle passageway of the lumen 102 or 104 into which it is intended to be inserted, without significant resistance, when the upper and middle passageway of the lumen 102 or 104 is without a blockage, obstruction, or other compromise.

In certain embodiments, the outer diameter of the body portion 12 of the LTFMD can taper similarly to part or all of the upper and middle passageways of the main or secondary lumen 102 or 104 of the NG tube 100 into which it is to be inserted.

The distal tip portion 16 is attached to the distal end of the body portion 12 and is uniquely contoured and configured to traverse the upper, middle, and lower end passageways of the main or secondary lumens 102 or 104 of the NG tube 100 into which the apparatus 10 is intended to be fully inserted.

The outer diameter of the distal tip portion 16 of the LTFMD 10 may be dependent on the inner diameter of the upper, middle, and lower passageways of the lumen 102 or 104 of the NG tube 100 into which it is intended to be inserted and on the intended task or purpose of the apparatus 10. However, the outer diameter of the distal tip portion 16 of the LTFMD 10 is preferably small enough to allow the tip portion 16 to traverse the proximal, middle, and distal passageways of the main or secondary lumens 102 or 104 of the NG tube 100 into which it is to be inserted, without significant resistance, when the upper, middle, and lower passageways of the lumen 102 or 104 is without a blockage, obstruction, or compromise.

Figure 11:
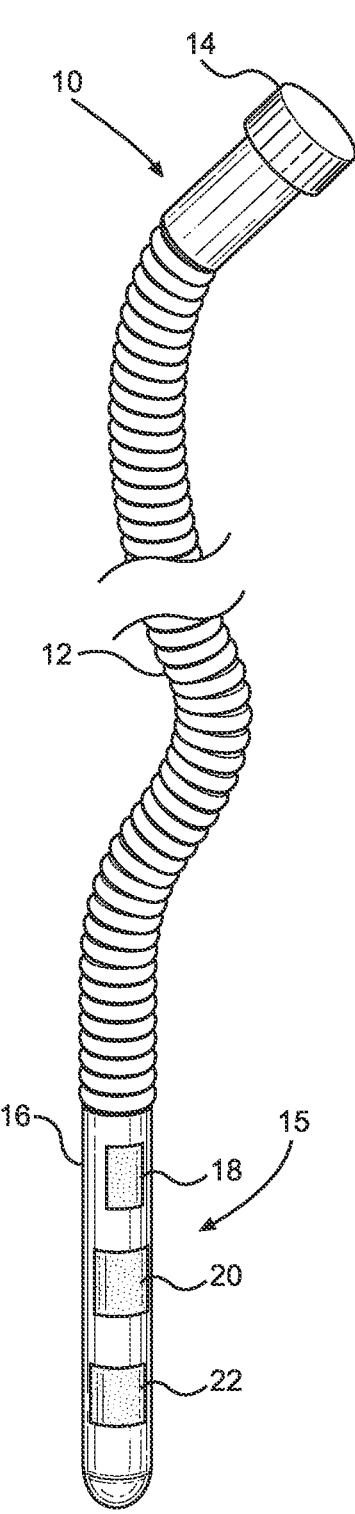
FIGS. 11, 12, 13, 14, and 15 are views in front elevation of alternative embodiments of the apparatus of the present invention.
Figure 12:
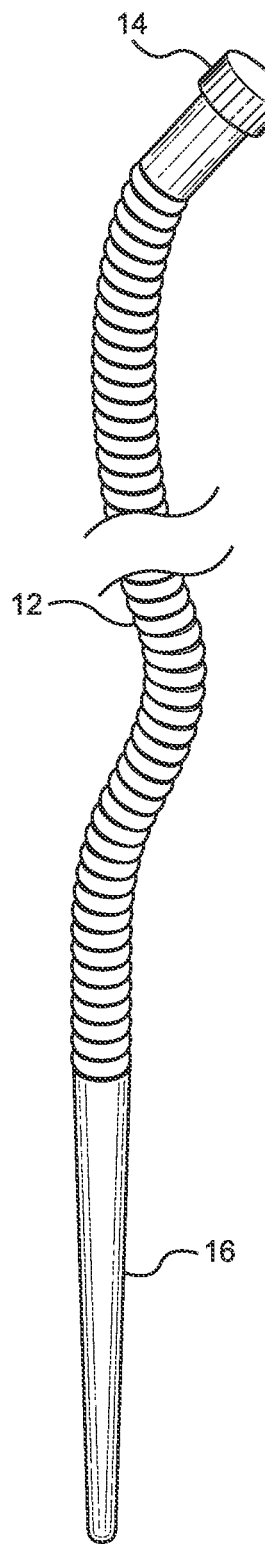
Figure 13:
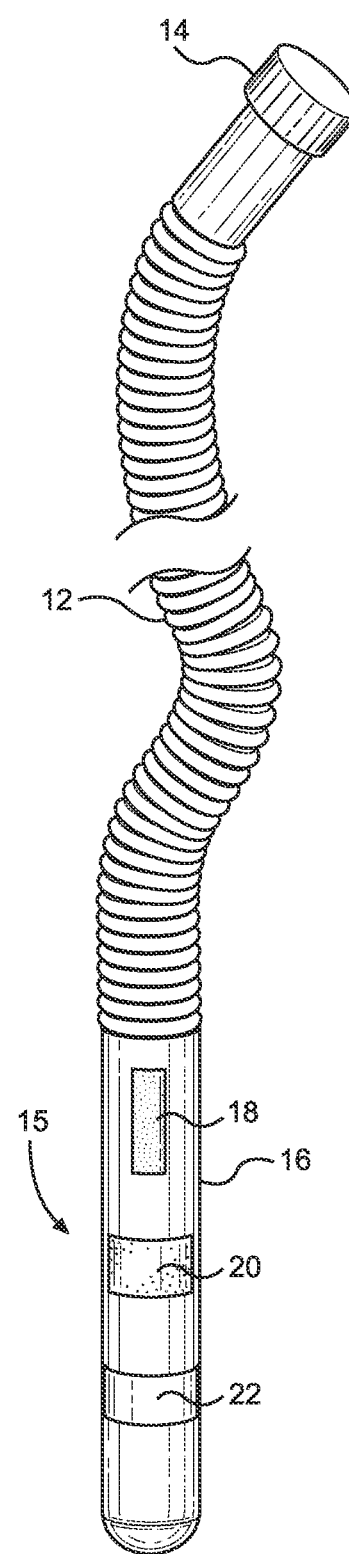

The distal tip portion 16 of the LTFMD 10 is not sharp. It may be blunt, flat, rounded, or otherwise shaped. In FIGS. 1, 11, and 13, for instance, the distal tip portion 16 is an elongate, rounded oblong shape. In FIGS. 2 and 12, for example, the distal tip portion 16 is tapered to a rounded end.

The body portion 12 of the LTFMD 10 has a first length and the distal tip portion 16 of the LTFMD 10 has a second length. The first length is normally greater than the second length. The combined lengths of the body portion 12 and the distal tip portion 16 of the LTFMD 10 will typically not exceed the full length of the passageway of the lumen 102 or 104 of the NG tube 100 in which it is to be inserted. However, the combined length of the body portion 12 and distal tip portion 16 of the LTFMD 16 will ideally be long enough to extend entirely or substantially entirely the length of the passageway of the lumen 102 or 104 of the NG tube 100 in which it is to be inserted. The combined length of the body portion 12 and the distal tip portion 16 of a LTFMD 10 will ideally be sufficient to permit, when the apparatus 10 can be fully inserted in a lumen 102 or 104, enough of the passageway of the lumen 102 or 104 will have been traveled and probed by the apparatus 10 to confirm that the lumen 102 or 104 does not have a blockage, obstruction or other compromise.

Figure 10:
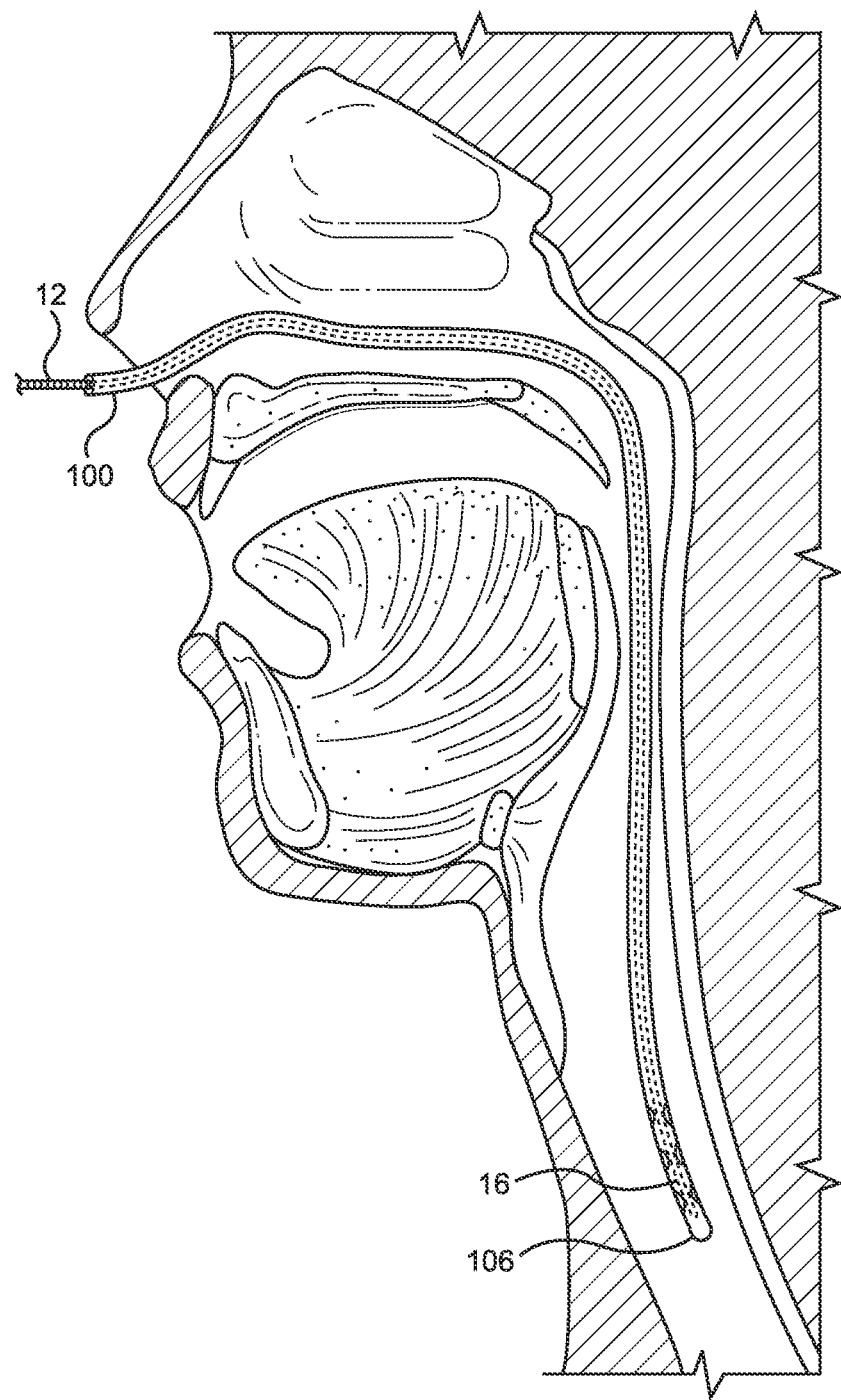
FIG. 10 is a view of an apparatus as disclosed herein operating to assist the NG tube during insertion and overcoming friction and resistance points within the NG tube.

According to embodiments of the invention, the length of the LTFMD 10 will be sufficient to perform a plurality of tasks. More particularly, the LTFMD 10 has a length sufficient that, when the apparatus 10 is fully inserted in the passageway of a lumen 102 or 104 of an NG tube 100 as in FIG. 10, for instance, the presence of the distal tip portion 16 of the apparatus 10 inside the distal portion 106 of the NG tube 100 permits the distal tip portion 16 of the apparatus 10 and the distal portion 106 of the NG tube 100 to work in concert, mutually assisting in navigating the terrain during insertion. Moreover, the length of the LTFMD 10 is sufficient that, when the apparatus 10 is fully inserted in the passageway of a lumen 102 or 104 of an NG tube 100, the apparatus 10 ensures that enough of the passageway of the lumen 102 or 104 has been traveled and probed to prove that the lumen 102 or 104 does not have a blockage, obstruction, or compromise. It will thus be understood that the actual length of the LTFMD 10 will then be determined based on the full length of the passageway of the lumen 102 or 104 of the NG tube 100 in which it will be inserted.

Still further, the LTFMD 10 has a length sufficient that, when the apparatus 10 is fully inserted in a lumen 102 or 104 of an NG tube 100 that is believed to be satisfactorily inserted in a person, the distal tip portion 16 of the apparatus 10, when incorporating one or more pH indicator sensors as taught herein and further described hereinbelow, is able to confirm whether the distal portion 106 of the NG tube 100 is in fact located in the stomach of the person.

When a LTFMD 10 according to the invention is fully inserted in a lumen 102 or 104 of an NG tube 100 before or after the distal portion 106 of the tube 100 is inserted in the nose of a person and then satisfactorily advanced, the person is not hindered or harmed by the presence of the LTFMD 10.

In one or more non-limiting embodiments where a purpose of the distal tip portion 16 of the LTFMD 10 is to assist the lower end of an NG tube 100 in traversing the terrain of the pathway from the nose to the stomach in a person during the insertion phase, the distal tip portion 16 of the LTFMD 10 is configured to be sufficient in diameter and rigidity such that the LTFMD 10, when fully inserted into the NG tube 100, adds firmness to the distal portion 106 of the NG tube 100 sufficient to prevent the distal portion 106 of the NG tube 100 from deviating or compromising when it encounters, for instance, friction or resistance points along the insertion path but not so much firmness and rigidity as to prevent the flexibility required of the NG tube 100 to permit insertion.

Figure 8:
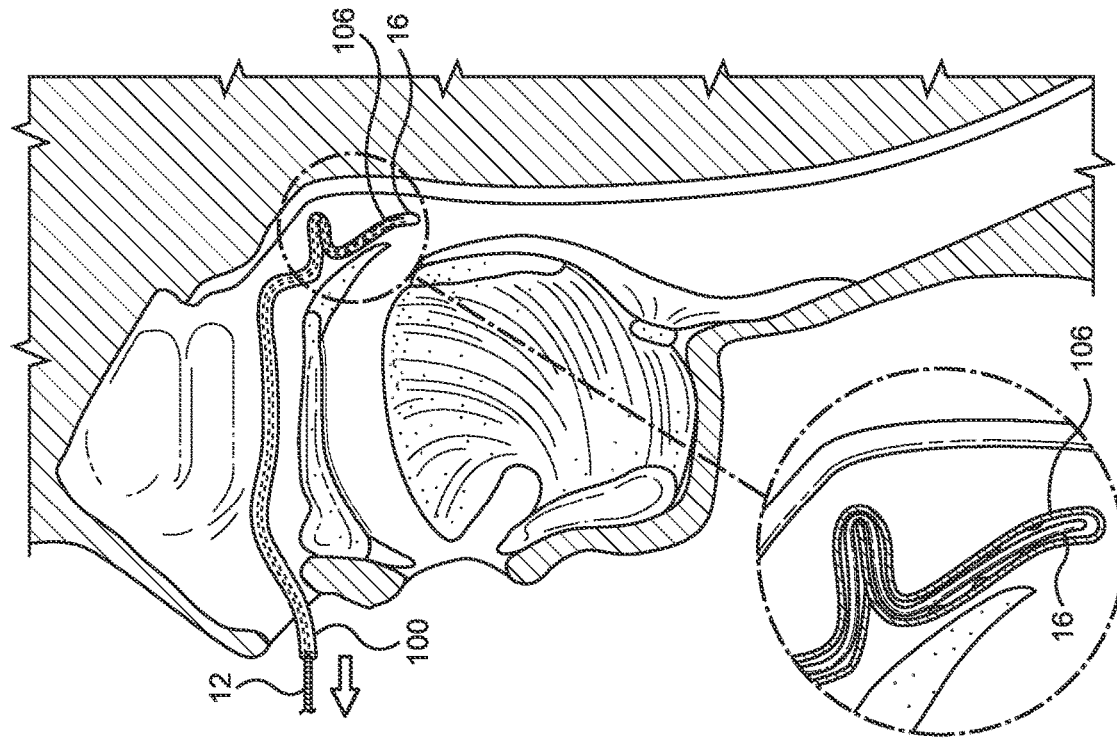
FIG. 8 is a view of an apparatus as disclosed herein with the advancement thereof obstructed by a compromise in the NG tube.
Figure 9:
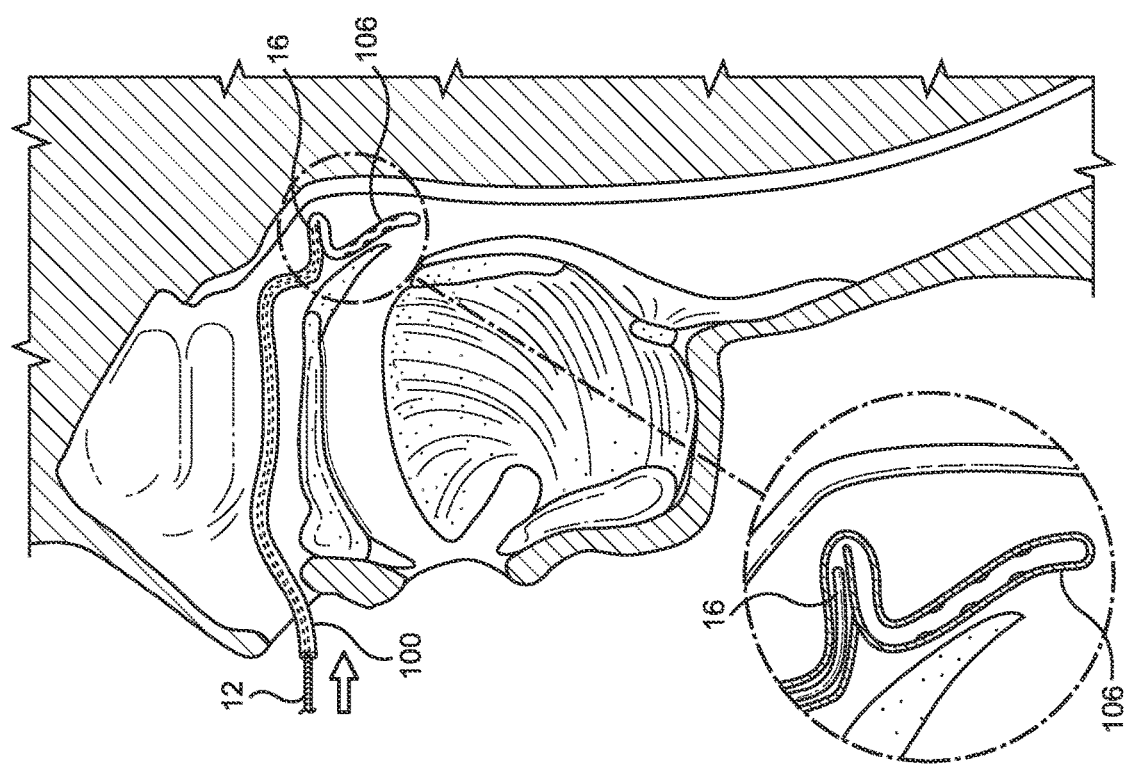
FIG. 9 is a view of an apparatus as disclosed herein with the retraction thereof prevented by a compromise in the NG tube.

In practices of the invention, a purpose of the LTFMD 10 is to check the passageway of a lumen 102 or 104 of an NG tube 100 for a blockage, obstruction, or other compromise as exists, for example, in FIG. 8. The outer diameter of the body portion 12 and, additionally or alternatively, the distal tip portion 16 of the LTFMD 10 is configured to be sufficiently large that, when the inner diameter of the passageway of the lumen 102 or 104 in which it is to be inserted is reduced smaller than the outer diameter of the body and distal tip portions 12 and 16 of the LTFMD 10, a user cannot insert the LTFMD 10 beyond the reduced inner diameter passageway of the lumen 102 or 104 without restriction by blockage, obstruction, or other compromise, assuming the LTFMD 10 is not already inserted in the lumen 102 or 104 prior to the reduction. Moreover, where a compromise comes to exist with the LTFMD 10 fully inserted into the NG tube 100 as in FIG. 9, the reduction in the inner diameter of the NG tube 100 tends to prevent retraction of the LTFMD 10 relative to the NG tube 100 thereby again providing a positive indication that an obstruction exists in the NG tube 100.

Resistance during the insertion attempt is thus an affirmative indication to the user that the passageway of the lumen 102 or 104 into which the user is attempting to insert the apparatus 10 is either blocked, obstructed, or compromised. Based on this affirmative indication, the user will likely remove the NG tube 100 from inside the person and restart the insertion process. The LTFMD 10 with the sufficiently large diameter described above is capable of producing this positive indication immediately after an NG tube 100 has been believed to be satisfactorily inserted without a need for the use of x-rays.

Figure 14:
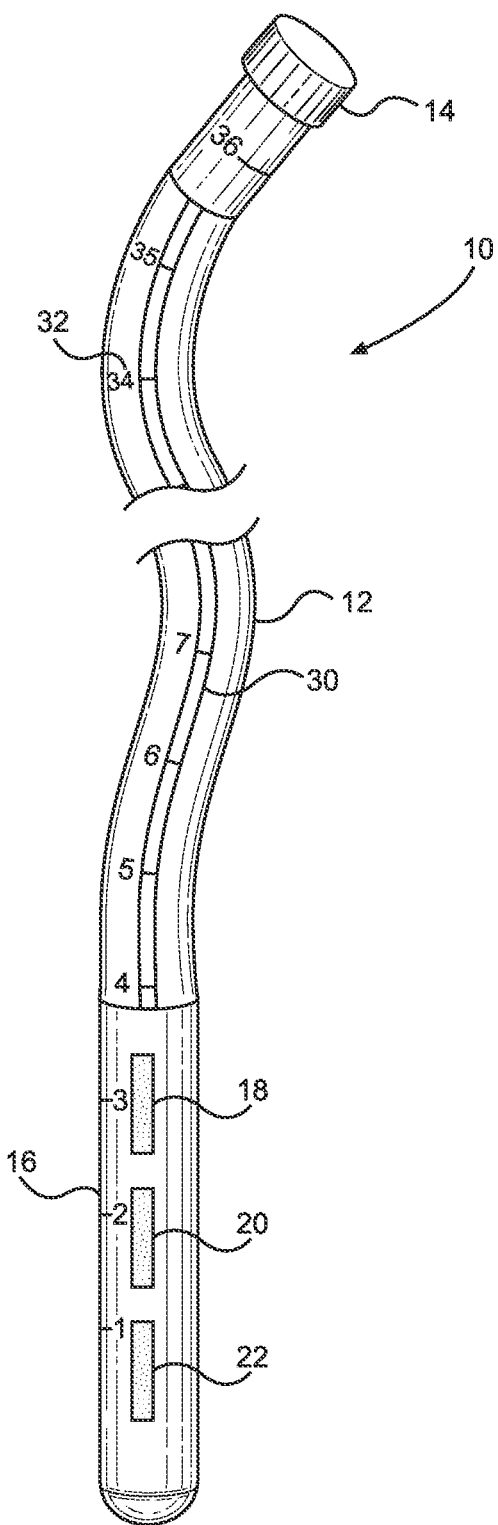

In certain embodiments, as depicted in FIG. 14, the outer surface of the LTFMD 10, such as the outer surface of the body portion 12, has at least one longitudinal reinforcing rib or raised bar 30 attached thereto that increases the thickness and effective outer diameter of the apparatus 10 at the location of the rib or raised bar 30. The increase in thickness of the outer diameter of the LTFMD 10 created by the presence of the rib or raised bar 30 increases the resistance of the apparatus 10 at the location of the rib or raised bar 30 when the apparatus 10 is being inserted in or removed from a lumen 102 or 104 of an NG tube 100 that has a blockage, obstruction or kink or twist type of compromise.

Figure 15:
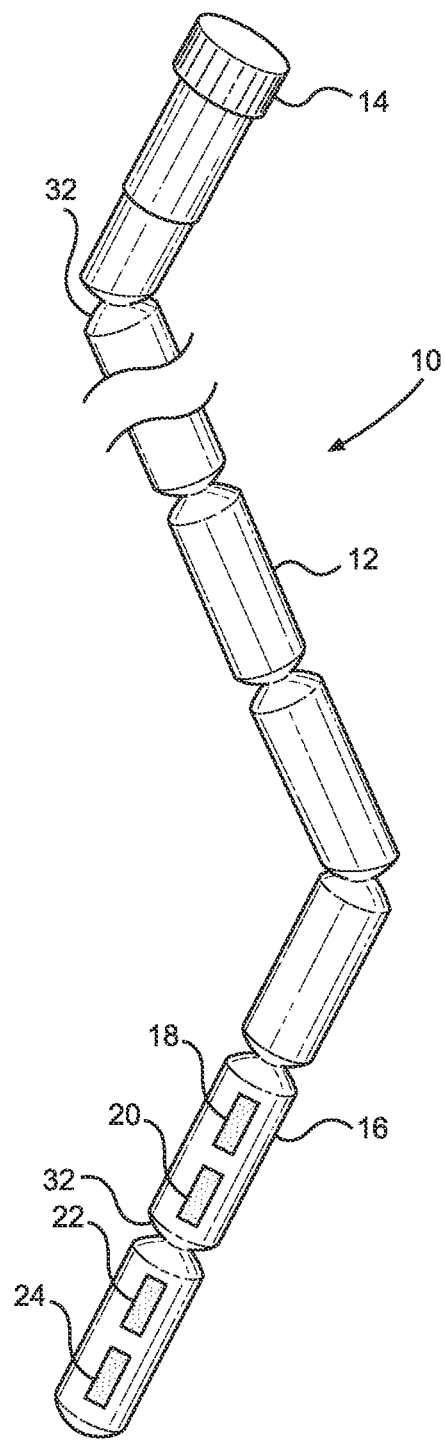

In non-limiting embodiments, as depicted in FIG. 15, the sheath 28 of the body portion 12 or the distal tip portion 16 of the LTFMD 10 has one or more notches 32 in the form of an indentation or incision in the body portion 12 or the distal tip portion 16. The notch 32 demonstrates decreased resistance to flexion in comparison to segments of the long, thin, flexible structure formed by the body portion 12 or the distal tip portion 16 disposed adjacent to the notch 32. The notch 32 thus causes the body portion 12 or the distal tip portion 16 to bend and form an angle between the two segments adjacent to the notch 32 rather than continuing the form of a curve when flexed in the vicinity of the notch 32, such as when encountering a curve while traversing the passageway of a lumen 102 or 104 of an NG tube 100. The angle formed by the bending between the segments to opposed sides of the notch 32 tends to cause the segments to opposite sides of a notch to straighten or remain straight and disposed in different directions. The straightened segments disposed along different directions make it difficult for the apparatus 10 to traverse the curviness of a lumen 102 or 104 that has formed a coil or loop type of compromise. Multiple notches 32 in the body portion 12 and, additionally or alternatively, the distal tip portion 16, which notches 32 may be separated by equal distance or unequal distances, will make it even more difficult for the straightened segments or portions of the LTFMD 10 to traverse the passageway of a lumen 102 or 104 that has formed a coil or loop type of compromise.

The LTFMD 10 can additionally include one or more measurement markings, scale, or demarcations 34 on the body portion 12 and the distal tip portion 16 of the apparatus 10 as is illustrated in FIG. 14. With that, the user can readily identify the full length of the LTFMD 10 minus the handle portion 14. By way of non-limiting example, embodiments of the LTFMD 10 have a numbering scale comprising measurement markings 34 arranged on the body portion 12 and the distal tip portion 16 wherein a highest number is disposed adjacent to the proximal end of the body portion 12 with progressively decreasing numbers toward and over the distal tip portion 16. Under such constructions, where a user is unable to insert the distal tip portion 16 and the body portion 12 into the lumen 102 or 104 of the NG tube 100 fully after the NG tube 100 is believed to be satisfactorily and fully inserted into a person as in FIG. 8, for example, the numbering scale 34 indicates how deep the blockage, obstruction, or compromise of the tube 100 is inside the person. For instance, the blockage, obstruction, or compromise can be indicated to be equal to the first visible number seen on the LTFMD 10 adjacent to the proximal entrance opening 110 or 112 of the lumen 102 or 104.

As shown, for instance, in FIGS. 1-6, 11, and 13, the LTFMD 10 can further incorporate one or more pH sensors to form a pH sensor array 15 to facilitate the rapid detection of whether an NG tube 100 in which the apparatus 10 is inserted has indeed been successfully placed in the stomach. As used herein, the term "pH" has the meaning normally associated with it in the field of chemistry: the "power of hydrogen," which is a measurement of the hydrogen ion concentration. A pH level is indicative of the degree of acidity or alkalinity in a fluid. The pH scale ranges from 1 to 14. A pH of 7 is considered to be neutral, a pH of 1 is totally acidic, and a pH of 14 is completely alkaline.

pH indicators are known wherein a halochromic chemical compound is added in small amounts to solutions so that the pH of the solution can be determined visually. A pH indicator detects the presence of H+ and OH−. It does this by reacting with H+ and OH−, which are themselves weak acids and bases. If an indicator is a weak acid and its conjugate base has a different color, deprotonation causes a color change.

It is further known that the human body comprises different bodily fluids, each with a characteristic and a different pH value. A pH indicator soaked and dried on a color or non-color filter paper will turn a verifiable color when it comes in contact with a fluid being tested. For example, Table 1 provides a small representative, but non-limiting, list of common pH indicators used in medicine.

TABLE 1

| Common pH Indicators | | |
| --- | --- | --- |
| Indicator | Acid Color | Base Color |
| Bromothymol Blue | Yellow | Blue |
| Phenol red | Yellow | Red |
| Phenolphthalein | Colorless | Magenta |

Gastric acid, gastric juice, or stomach acid is a digestive fluid formed only in the stomach and is composed of hydrochloric acid, potassium chloride, and sodium chloride. Since acid-base pH indicators are solutions that have a characteristic color at certain pH levels, they can be used to visually signal the acidity of an aqueous (water-based) solution, such as gastric acid.

Alkaline mucus is a thick fluid produced by mammals. It confers tissue protection in an acidic environment, such as in the stomach. Alkaline mucus has a characteristic color at certain pH levels and can be used to visually signal the alkalinity of an aqueous (water-based) solution in the stomach.

Filter paper material is a semi-permeable paper barrier that is typically placed perpendicular to a liquid or air flow. All filter paper materials have various properties. Important parameters include wet strength, porosity, particle retention, volumetric flow rate, efficiency, and capacity. There are two mechanisms of filtration with paper: volume and surface. By volume filtration, the particles are caught in the bulk of the filter paper. By surface filtration, the particles are caught on the paper surface. Filter paper materials may therefore be considered advantageous since even a small piece of filter paper will absorb a significant volume of liquid, such as gastric acid.

Porous materials, such as gauze, are a thin, translucent fabric of silk, linen, cotton, or a very fine wire mesh. Porous materials also have two mechanisms of filtration and can be used like filter paper materials because even a small piece of gauze will absorb a significant volume of liquid, such as gastric acid.

According to embodiments of the invention, the distal portion of the LTFMD 10, such as the distal tip portion 16 thereof, can include a pH sensor array 15 comprising one or more swabs or sensors 18, 20, 22, and 24. In the embodiment of FIG. 1, for instance, the pH sensor array 15 includes three swabs or sensors 18, 20, and 22. In the embodiments of FIGS. 3 and 4, for example, the pH sensor array 15 includes four swabs or sensors 18, 20, 22, and 24. Each swab or sensor 18, 20, 22, and 24 can incorporate a pH indicator. For avoidance of doubt, a pH sensor array 15 could include just a single swab or sensor 18. The pH indicators of the sensors 18, 20, 22, and 24 can be the same or different, calibrated to check for the same liquid or different liquids. Each swab or sensor 18, 20, 22, and 24 can be composed completely or partially of filter paper, gauze, or any porous or other material capable of retaining a pH indicator, such as by being soaked therein. Swabs or sensors 18, 20, 22, and 24 can be retained in any manner, such as by being attached to the distal tip portion 16 of the LTFMD 10 by glue, adhesive paper, spray adhesive, or any known method capable of bonding the two together.

When a LTFMD 10 with a pH sensor array 15 incorporated into the distal tip portion 16 is fully inserted in the main lumen 102 of an NG tube 100 as, for instance, in FIGS. 4 and 6, the pH sensor array 15 can be disposed to be aligned with the eyelet openings 108 in the distal portion 106 of the main lumen 102. The alignment of the pH indicator sensors 18, 20, 22, and 24 of the pH sensor array 15 in the distal portion 106 of the LTFMD 10 with the eyelet openings 108 in the distal portion 106 of the main lumen 102 ensures a user that fluid surrounding the main lumen 102 that passes through an eyelet opening 108 will make contact with a pH indicator sensor 18, 20, 22, and 24 of the pH sensor array 15. The result of the contact between the fluid and the pH indicator sensors 18, 20, 22, and 24 of the pH sensor array 15 produces a verifiable color change confirming either that the fluid that made contact with the pH indicator sensor is the fluid being searched for by the pH indicator or, where there is no change in color, that the fluid being searched for by the pH indicator has not been contacted.

When a LTFMD 10 with a pH sensor array 15 incorporated in the distal tip portion 16 is fully inserted in the secondary lumen 104 of an NG tube 100 as in FIGS. 3 and 5, for example, the pH sensor array 15 will be aligned or disposed as closely as possible relative to an opening 114 in the distal portion 106 of the NG tube 100 between the main lumen 102 and the secondary lumen 104. The alignment of the pH sensor array 15 at the distal portion 106 of the LTFMD 10 with the opening 114 at the distal end of the secondary lumen 104 ensures a user that fluid surrounding the distal portion 106 of the LTFMD 10 that passes through the eyelet openings 108 will pass through the opening 114 to make contact with the pH indicator sensors 18, 20, 22, and 24 of the pH sensor array 15. The result of the contact between the surrounding fluid and the pH indicator sensors 18, 20, 22, and 24 will either produce a verifiable color change or no change in color, again positively confirming whether the fluid that made contact with the pH indicator sensors 18, 20, 22, and 24 is the liquid being searched for by the pH indicator.

Accordingly, a LTFMD 10 incorporating a pH sensor array 15 can be used to test for, without limiting the applicability of the invention except as the claims expressly require, the presence of gastric acid, alkaline, and other fluids found in the digestive system or lungs of a person.

In certain embodiments where a purpose of the LTFMD 10 is to confirm the placement of the distal portion 106 of the main lumen 102 of the NG tube 100 inside a person as in FIG. 4, for example, the distal tip portion 16 of the LTFMD 10 retains one or more pH acidic base indicator sensors 18, 20, 22, and 24. The diametrical size and configuration of the body portion 12 and the distal tip portion 16 of the apparatus 10 can be much smaller than the diametrical size of the body portion 12 and distal tip portion 16 that would be used in this same main lumen 102 if the purpose of the apparatus 10 were to assist during insertion or in checking for a blockage, obstruction, or compromise. The smaller diametrical size of the body portion 12 and distal tip portion 16 of the LTFMD 10 will give the LTFMD 10 the ability to be inserted and removed by the user quickly and without significant interference or resistance since the only concern is to have the distal tip portion 16 of the apparatus 10 make contact with the fluid that enters the distal portion 106 of the NG tube 100.

Embodiments of the invention can, for instance, have plural pH indicator sensors 18, 20, and 22 retained by the distal tip portion 16 as in FIG. 11. As in the depicted embodiment, the sensors 18, 20, and 22 of the array 15 of pH indicator sensors can be spaced in longitudinal alignment along the distal tip portion 16. At least two of the pH indicator sensors 18, 20, and 22 can incorporate different types of pH indicators. The pH sensors 18, 20, and 22 can be located in different areas on the distal tip portion 16 or elsewhere on the LTFMD 10. For instance, a first pH sensor 18 could be located on the upper half of the distal tip portion 16 and can retain a pH alkaline base indicator, a third pH indicator sensor 22 can be located on the lower half of the distal tip portion 16 and can retain a pH acidic base indicator, and a second pH indicator sensor 20 can be disposed between the first and third sensors 18 and 22 and can retain a pH alkaline base indicator, a pH acidic base indicator, or some other test indicator. Such multi-pH indicator sensor embodiments allow a user to test for the presence of two different body fluids simultaneously thereby saving time, money, and discomfort to a person.

In certain practices, the LTFMD 10 can be employed when an NG tube 100 without a LTFMD 10 inside a lumen 102 or 104 is inserted in a person and then an x-ray is taken to locate the distal portion 106 of the NG tube 100 showing that the distal portion 106 of the NG tube 100 is much farther down inside the stomach than desired and needs to be pulled back several centimeters. After the NG tube 100 has been pulled back several centimeters, the user may not wish to radiate the person again by x-rays just to check the retracted location of the distal portion 106 of the NG tube 100, but the user is interested in confirming that the distal portion 106 of the NG tube 100 is still inside the stomach. The user may then choose to insert a LTFMD 10 configured with a body portion 12 and distal tip portion 16 of equal outer diameters both much smaller than the diametrical size that would be used to check for a compromise in the lumen 102 or 104 into which it is to be inserted. The smaller outer diameter of the LTFMD 10 will allow the body and distal tip portions 12 and 16 to traverse the lumen 102 or 104 faster and without interference. The LTFMD 10 can incorporate one or more pH acidic base indicator sensors 18, 20, 22, and 24 in the distal tip portion 16.

With such an LTFMD 10 provided, the user can fully insert the LTFMD 10 with the pH acidic base indicator sensor or sensors 18, 20, 22, and 24 retained by the distal tip portion 16 into the main lumen 102 of the NG tube 100. Fluid that enters the eyelet openings 108 in the distal portion 106 of the main lumen 102 from the surrounding area outside the NG tube 100 will then make contact with the pH acidic base indicator sensors 18, 20, 22, and 24 at the distal tip portion 16 while disposed in the distal portion 106 of the main lumen 102 and, ideally, aligned with the eyelet openings 108 as shown, for instance, in FIG. 4. A verifiable color change, or conversely no change in color, of the pH acidic base indicator sensor or sensors 18, 20, 22, and 24 will positively indicate whether the lower end of the main lumen 102 of the NG tube 100 is still inside the stomach after being retracted several centimeters. This confirmation can be made in seconds, and the delay, cost, inconvenience, and excess radiation deriving from further x-ray procedures are avoided.

Also according to embodiments of the invention, after a user has fully inserted an NG tube 100 without a LTFMD 10 inside a lumen 102 or 104 into a person and then the person develops a persistent cough, the user may become concerned regarding whether the NG tube 100 has veered off course and landed inside a lung of the person instead of the stomach. There are two ways the user can check the location of the NG tube 100 inside the person using the LTFMD 10 instead of using x-rays.

One way is for the user to choose a LTFMD 10 that is incorporated with one or more pH acidic base indicator sensors 18, 20, 22, and 24 at the distal tip portion 16. The diameters of the body portion 12 and the distal tip portion 16 of the LTFMD 10 are small enough to traverse the passageway of the main lumen 102 of the NG tube 100 in which it will be inserted. With such an LTFMD 10 provided, the user fully inserts the LTFMD 100 with the pH acidic base indicator sensor or sensors 18, 20, 22, and 24 then disposed in the distal portion 106 of the NG tube 100. The fluid that enters the eyelet openings 108 in the distal portion 106 of the main lumen 102 from the surrounding area outside the NG tube 100 makes contact with the pH acidic base indicator sensor or sensors 18, 20, 22, and 24 retained by the distal tip portion 16 of the LTFMD 10. The user can then turn the handle 14 of the LTFMD 10 clockwise and counter-clockwise and retract and advance the apparatus 10 several times to help fluid inside the distal portion 106 of the NG tube 100 make contact with the pH indicator sensor or sensors 18, 20, 22, and 24 of the apparatus 10. The user can then completely remove the LTFMD 10 from the main lumen 102 of the NG tube 100 and visually review the pH indicator sensor or sensors 18, 20, 22, and 24 at the distal tip portion 16. A verifiable color change or a lack of a color change of the pH acidic base indicator sensor or sensors 18, 20, 22, and 24 of the color being searched for will positively indicate whether the distal portion 106 of the main lumen 102 of the NG tube 100 is inside the stomach with, for instance, a verifiable color change indicating that the distal portion 106 is inside the stomach and a lack of a color change indicating that the distal portion 106 is not inside the stomach.

The second way the user can use the LTFMD 10 to confirm whether the NG tube 10 is in a lung or the stomach is for the user to choose a LTFMD 10 incorporated with a pH sensor array 15 with a pH indicator sensor or sensors 18, 20, 22, and 24 sensitive to the composition of lung fluid. In certain practices, the sensor array 15 can include one or more pH indicator sensors 18, 20, 22, and 24 sensitive to the composition of lung fluid and one or more pH indicator sensors 18, 20, 22, and 24 sensitive to gastric acid. In any event, the diameter of the body portion 12 and the distal tip portion 16 of the LTFMD 10 will be sufficiently small to traverse the passageway of the main lumen 102 of the NG tube 100 in which it will be inserted. The user fully inserts the LTFMD 10 with the pH indicator sensor or sensors 18, 20 22, and 24 sensitive to the composition of lung fluid to dispose the pH sensor array 15 in the distal portion 106 of the main lumen 102 of the NG tube 100. The fluid that enters the eyelet openings 108 in the distal portion 106 of the main lumen 102 of the NG tube 100 from the area surrounding the NG tube 100 makes contact with the pH indicator sensor or sensors 18, 20, 22, and 24 sensitive to the composition of lung fluid incorporated on the distal tip portion 16 of the LTFMD 10. The user can then turn the handle portion 14 of the LTFMD 10 clockwise and counter-clockwise and extend and retract the apparatus 10 several times to help fluid inside the distal portion 106 of the NG tube 100 to make contact with the pH indicator sensor or sensors 18, 20, 22, and 24. The user can then completely remove the LTFMD 10 from the lumen 102 or 104 of the NG tube 100 and visually review the pH indicator sensor or sensors 18, 20, 22, and 24 of the distal tip portion 16. A verifiable color change of the pH indicator sensor or sensors 18, 20, 22, and 24 sensitive to the composition of lung fluid of the color being searched for will confirm whether the distal portion 106 of the main lumen 102 of the NG tube 100 is inside a lung with, for instance, a verifiable color change indicating that the distal portion 106 is inside a lung and a lack of a color change indicating that the distal portion 106 is not inside a lung.

Where applicable, a verifiable color change of the pH indicator sensor or sensors 18, 20, 22, and 24 sensitive to the gastric acid will confirm whether the distal portion 106 of the main lumen 102 of the NG tube 100 is inside the stomach. Both of the above methods using the LTFMD 10 will result in a positive confirmation for the user and can be performed in seconds after an NG tube 100 is inserted without a delay and without radiating the person with an x-ray.

The same diameter LTFMD 10 and steps described above can be used when a user inserts an NG tube 100 without a LTFMD 10 inside a lumen 102 or 104 into a person and the person develops a persistent cough after the insertion. In such an instance, the user may become concerned regarding whether the NG tube 100 veered off course and is now in a lung. The user can quickly insert a LTFMD 10 into the lumen 102 or 104 of the NG tube 100 to obtain a positive indication of the location of the distal portion 106 of the NG tube 100 based on the color change or lack of color change of the pH indicator sensor or sensors 18, 20, 22, and 24 of the pH sensor array 15.

In one or more non-limiting embodiments, a two-prong approach using the LTFMD 10 may be practiced by a user. There are times in medicine when, after the insertion of a two-lumen NG tube 10 is confirmed by an x-ray, the main or suction lumen 102 of the NG tube 100 is then connected to a suction device (not shown). Sometime later, suctioning through the NG tube 100 appears to a user to be sluggish and erratic. In this situation, the main or suction lumen 102 of the NG tube 100 can remain connected to the suction device while the user selects a first LTFMD 10, such as the LTFMD 10 depicted in FIG. 12, configured with a sufficiently large diameter to be capable of checking the secondary lumen 104 of the tube 100 for a compromise. The user seeks to determine if the tube 100 has become blocked, obstructed, or compromised and is the reason for the erratic suctioning behavior. The user inserts the distal tip portion 16 of a first LTFMD 10 into the secondary lumen 104 of the NG tube 100 and advances the apparatus 100 in the lumen 104. If the user is able to insert the full length of the first LTFMD 10 inside the secondary lumen 104 without resistance from a blockage, obstruction, or other compromise, this is a positive sign to the user that the secondary lumen 104 does not have a blockage, obstruction, or other compromise, and whether the main lumen 102 of the NG tube 100 has a compromise or another reason for the erratic suctioning behavior must be considered.

Being successful in fully inserting the first LTFMD 10 into the secondary lumen 104, the user may next decide to disconnect the main lumen 102 of the NG tube 100 from the suction device in an effort to see if the main lumen 102 is partially blocked or obstructed by a solid object such as a clot or food particle that can be the cause for the erratic suctioning behavior. This time, the user may select a second LTFMD 10, such as that depicted in FIG. 2 or 13, configured with a much larger diameter than the diameter of the first LTFMD 10 but still small enough to traverse the main lumen 102 of the NG tube 100 with resistance or interference when the lumen 102 is without a blockage or obstruction. The larger diameter corresponds to the larger diameter of the main lumen 102 as compared to the secondary lumen 104. The body portion 12 and the distal tip portion 16 of the second LTFMD 10 both have the larger diameter. The second LTFMD 10 may or may not have a pH sensor array 15. The user inserts the second LTFMD 10 with the much larger diameter into the main lumen 102 of the NG tube 100 to check if the main lumen 102 is partially blocked or obstructed by a solid object. If the entire length of the second LTFMD 10 is able to be fully inserted in the main lumen 102 of the NG tube 100 by the user without resistance from a blockage, obstruction, or other compromise, this is a positive indication that the erratic suctioning behavior is not due to a blockage or obstruction inside the main lumen 102 of the tube 100. The user must consider another reason for the erratic suctioning behavior.

Apparatuses 10 according to the present invention may be packaged in multiple different ways. For instance, apparatuses 10 may be packaged as individual units and may be specified for the main lumen 102 or the secondary lumen 104 of NG tubes 100 of specific dimensions. In other practices, LTFMDs 10 as disclosed herein may be packaged in bulk. Still further, the LTFMD 10 may be packaged as a kit and system that includes at least one LTFMD 10 according to the present invention and at least one NG tube 100. The at least one LTFMD 10 and the at least one NG tube 100 may be sized in correspondence, such as for the LTFMD 10 to be received into the main lumen 102 of the NG tube 100, for the LTFMD 10 to be received into the secondary lumen 104 of the NG tube 100, or with first and second LTFMDs 10 sized to be received into the main and secondary lumens 102 and 104 respectively. Such kits or systems may be packaged in sterile disposable or recyclable packaging.

It will be understood that terms of orientation, nomenclature, and other conventions used herein merely provide a complete understanding of the disclosed invention and are not limiting. Other conventions may be used without limitation of the teachings herein. Furthermore, the various components disclosed herein are merely illustrative and are not limiting of the invention. For example, except as limited by the claims, each of the components and steps discussed herein may include subcomponents or substeps that collectively provide for the structure and function of the disclosed component or step. Still further, one or more components or steps, sometimes referred to as members or otherwise herein, could be combined as a unitary structure or a single step while still corresponding to the disclosed components or steps. Additional components and steps that provide additional functions, or enhancements to those introduced herein, may be included. For example, additional components, steps, and materials, combinations of components, steps, or materials, and perhaps the omission of components, steps, or materials may be used to create embodiments that are nonetheless within the scope of the teachings herein When introducing elements of the present invention or embodiments thereof, the articles "a," "an," and "the" are intended to mean that there are one or more of the elements. The terms "comprising," "including," and "having" are intended to be inclusive such that there may be additional elements other than the listed elements. As used herein, the term "example" or "exemplary" is not intended to imply a superlative example. Rather, "exemplary" refers to an embodiment that is one of many possible embodiments.

With certain details and embodiments of the present invention for methods and apparatuses for assisting, checking, and confirming nasogastric and orogastric tube insertion and placement disclosed, it will be appreciated by one skilled in the art that numerous changes and additions could be made thereto without deviating from the spirit or scope of the invention. This is particularly true when one bears in mind that the presently preferred embodiments merely exemplify the broader invention revealed herein. Accordingly, it will be clear that those with major features of the invention in mind could craft embodiments that incorporate those major features while not incorporating all of the features included in the preferred embodiments.

Therefore, the following claims shall define the scope of protection to be afforded to the inventor. Those claims shall be deemed to include equivalent constructions insofar as they do not depart from the spirit and scope of the invention. A plurality of the following claims may express, or be interpreted to express, certain elements as means for performing a specific function, at times without the recital of structure or material. As the law demands, any such claims shall be construed to cover not only the corresponding structure and material expressly described in this specification but also all legally-cognizable equivalents thereof.

I claim the following as deserving of the protection of Letters Patent:

1. A kit for assisting in, checking, and confirming placement of a distal portion of a lumen of a gastric tube in a stomach of a mammal, the kit comprising:
    a gastric tube comprising a lumen with an entrance, a passageway, and a distal portion;
    a long, thin, flexible medical apparatus comprising an elongate body portion of flexible material, the body portion with a proximal end and a distal end, a handle portion fixed to the proximal end of the body portion, a distal tip portion fixed to the distal end of the body portion wherein the body portion and the distal tip portion together form a long, thin, flexible structure with a length for being selectively received into the passageway of the lumen of the gastric tube, and a pH indicator sensor array retained by the long, thin, flexible structure formed by the body portion and the distal tip portion wherein the pH indicator sensor array comprises a first pH indicator sensor with a pH indicator calibrated to exhibit a verifiable response to contact with a predetermined subject fluid;
    wherein the long, thin, flexible medical apparatus is adapted for being selectively inserted into and removed from the passageway of the lumen of the gastric tube whereby an ability to insert the body portion and the distal tip portion into the passageway in the lumen of the gastric tube over the length of the long, thin, flexible structure provides a positive indication that the lumen is not blocked, obstructed, or otherwise compromised over the length of the long, thin, flexible structure and whereby, when the long, thin, flexible medical apparatus is inserted into and removed from the passageway of the lumen of the gastric tube, the verifiable response or lack of the verifiable response of the pH indicator will positively indicate whether the pH indicator sensor has made contact with the predetermined subject fluid.

2. The apparatus of claim 1, wherein the distal tip portion of the apparatus has rigidity sufficient, when received into the distal portion of the lumen of the gastric tube, to facilitate passage of the distal portion of the lumen during insertion into the mammal.

3. The kit of claim 1, wherein the body portion and the distal tip portion of the apparatus have lateral dimensions sufficient to prevent retraction of the body portion and the distal tip portion when the body portion and the distal tip portion have been received into the lumen of the gastric tube and a compromise develops in the lumen of the gastric tube along the length of the long, thin, flexible structure.

4. The kit of claim 1, wherein the first pH indicator sensor is calibrated to exhibit a verifiable color change in response to contact with gastric fluid.

5. The kit of claim 1, wherein the first pH indicator sensor is calibrated to exhibit a verifiable color change in response to contact with lung fluid.

6. The kit of claim 1, wherein the pH indicator sensor array retained by the long, thin flexible structure further comprises a second pH indicator sensor with a pH indicator calibrated to exhibit a verifiable color change in response to contact with a predetermined subject fluid.

7. The kit of claim 6, wherein the first and second pH indicator sensors are calibrated to exhibit a verifiable color change in response to contact with the same predetermined subject fluid.

8. The kit of claim 7, wherein the first and second pH indicator sensors are calibrated to exhibit a verifiable color change in response to contact with the same predetermined subject fluid comprising gastric fluid.

9. The kit of claim 7, wherein the first and second pH indicator sensors are calibrated to exhibit a verifiable color change in response to contact with different predetermined subject fluids.

10. The kit of claim 9, wherein the first pH indicator sensor is calibrated to exhibit a verifiable color change in response to contact with gastric fluid and wherein the second pH indicator sensor is calibrated to exhibit a verifiable color change in response to contact with lung fluid.

11. The kit of claim 1, wherein the pH indicator sensor array retained by the long, thin flexible structure comprises a plurality of pH indicator sensors, each with a pH indicator calibrated to exhibit a verifiable color change in response to contact with a predetermined subject fluid, wherein the plurality of pH indicator sensors are spaced in longitudinal alignment along the long, thin, flexible structure.

12. The apparatus of claim 1, further comprising measurement markings disposed along the long, thin, flexible structure.

13. The apparatus of claim 12, wherein the measurement markings descend along the long, thin, flexible structure from a highest number is disposed adjacent to the proximal end of the body portion.

14. The apparatus of claim 1, further comprising at least one notch in the long, thin, flexible structure wherein the at least one notch demonstrates decreased resistance to flexion in comparison to segments of the long, thin, flexible structure disposed adjacent to the notch.

15. The apparatus of claim 1, further comprising at least one longitudinal reinforcing rib disposed on the long, thin, flexible structure wherein the reinforcing rib increases the local thickness and rigidity of the long, thin, flexible structure.

16. The kit of claim 1, wherein the body portion comprises an elongate core surrounded by a sheath.

17. A kit for assisting in, checking, and confirming placement of a distal portion of a lumen of a gastric tube in a stomach of a mammal, the kit comprising:
 a gastric tube comprising a lumen with an entrance, a passageway, and a distal portion;
 a long, thin, flexible medical apparatus for being selectively inserted into and removed from the passageway of the lumen of the gastric tube, the long, thin, flexible medical apparatus comprising:
  an elongate body portion of flexible material, the body portion with a proximal end and a distal end;
  a handle portion fixed to the proximal end of the body portion; and
  a distal tip portion fixed to the distal end of the body portion wherein the body portion and the distal tip portion together form a long, thin, flexible structure with a length for being selectively received into the passageway of the lumen of the gastric tube;
 wherein the body portion and the distal tip portion of the apparatus have lateral dimensions sufficient to prevent passage of the body portion and the distal tip portion past a blockage, obstruction, or other compromise in the lumen of the gastric tube and wherein the body portion and the distal tip portion of the apparatus have lateral dimensions sufficient to prevent retraction of the body portion and the distal tip portion when the body portion and the distal tip portion have been received into the lumen of the gastric tube and a compromise develops in the lumen of the gastric tube along the length of the long, thin, flexible structure;
 whereby an ability to insert and withdraw the body portion and the distal tip portion in relation to the passageway in the lumen of the gastric tube over the length of the long, thin, flexible structure provides a positive indication that the lumen is not blocked, obstructed, or otherwise compromised over the length of the long, thin, flexible structure.

18. The kit of claim 17, wherein the distal tip portion of the apparatus has rigidity sufficient, when received into the distal portion of the lumen of the gastric tube, to facilitate passage of the distal portion of the lumen during insertion into the mammal.

19. The kit of claim 17, further comprising a pH indicator sensor array retained by the long, thin, flexible structure formed by the body portion and the distal tip portion wherein the pH indicator sensor array comprises a first pH indicator sensor with a pH indicator.

20. The kit of claim 19, wherein the first pH indicator sensor is calibrated to exhibit a verifiable color change in response to contact with a predetermined subject fluid.

21. The kit of claim 20, wherein the first pH indicator sensor is calibrated to exhibit a verifiable color change in response to contact with gastric fluid.

22. The kit of claim 20, wherein the first pH indicator sensor is calibrated to exhibit a verifiable color change in response to contact with lung fluid.

23. The kit of claim 19, wherein the pH indicator sensor array retained by the long, thin flexible structure further comprises a second pH indicator sensor with a pH indicator calibrated to exhibit a verifiable color change in response to contact with a predetermined subject fluid.

24. The kit of claim 23, wherein the first and second pH indicator sensors are calibrated to exhibit a verifiable color change in response to contact with the same predetermined subject fluid.

25. The kit of claim 24, wherein the first and second pH indicator sensors are calibrated to exhibit a verifiable color change in response to contact with gastric fluid.

26. The kit of claim 23, wherein the first and second pH indicator sensors are calibrated to exhibit a verifiable color change in response to contact with different predetermined subject fluids.

27. The kit of claim 26, wherein the first pH indicator sensor is calibrated to exhibit a verifiable color change in response to contact with gastric fluid and wherein the second pH indicator sensor is calibrated to exhibit a verifiable color change in response to contact with lung fluid.

28. The kit of claim 1, wherein the pH indicator sensor array retained by the long, thin flexible structure further comprises a plurality of pH indicator sensors, each with a pH indicator calibrated to exhibit a verifiable color change in response to contact with a predetermined subject fluid, wherein the plurality of pH indicator sensors are spaced along the long, thin, flexible structure.

29. The kit of claim 28, wherein the distal portion of the lumen of the gastric tube has a plurality of openings spaced therein and wherein the plurality of pH indicator sensors of the pH indicator sensor array are disposed to align with the plurality of openings in the distal portion of the gastric tube when the long, thin, flexible structure is inserted into the lumen of the gastric tube whereby the long, thin, flexible structure can be inserted into the lumen of the gastric tube to cause the plurality of pH indicator sensors of the pH indicator sensor array to align with the plurality of openings in the distal portion of the gastric tube and whereby the long, thin, flexible medical structure can be completely removed from the lumen of the gastric tube to obtain the verifiable color change or lack of the verifiable color change of the plurality of pH indicator sensors of the pH indicator sensor array to indicate whether the pH indicator sensors have made contact with the predetermined subject fluid.

30. The kit of claim 17, wherein the passageway of the lumen of the gastric tube has a length and wherein the length of the long, thin, flexible structure formed by the body portion and the distal tip portion does not exceed the length of the passageway of the lumen.

31. The kit of claim 30, wherein the length of the long, thin, flexible structure formed by the body portion and the distal tip portion is approximately equal to the length of the passageway of the lumen whereby an ability to insert the body portion and the distal tip portion of the long, thin, flexible medical apparatus into the passageway in the lumen of the gastric tube over the length of the long, thin, flexible structure provides a positive indication that the lumen is not blocked, obstructed, or otherwise compromised over the length of the long, thin, flexible structure and over the length of the passageway of the lumen.

32. The kit of claim 31, further comprising measurement markings disposed along the long, thin, flexible structure.

33. The kit of claim 29, wherein the plurality of pH indicator sensors are spaced in longitudinal alignment along the long, thin, flexible structure.

* * * * *

UNITED STATES PATENT AND TRADEMARK OFFICE
CERTIFICATE OF CORRECTION

| | | |
|---|---|---|
| PATENT NO. | : 11,304,877 B2 | |
| APPLICATION NO. | : 17/331966 | |
| DATED | : April 19, 2022 | |
| INVENTOR(S) | : Glenn Gerald Strawder | |

It is certified that error appears in the above-identified patent and that said Letters Patent is hereby corrected as shown below:

In the Specification

Column 3, Line 10: delete "drawing" and insert --drawings--.

Column 8, Line 55: delete "is" and insert --are--.

Column 10, Line 46: delete "10" and insert --104--.

Column 17, Line 53: insert --,-- after "20".

In the Claims

Column 21, Line 45, in Claim 13: delete "is".

Signed and Sealed this
Twelfth Day of July, 2022

*Katherine Kelly Vidal*

Katherine Kelly Vidal
*Director of the United States Patent and Trademark Office*